US011499963B2

(12) United States Patent
Iwao et al.

(10) Patent No.: US 11,499,963 B2
(45) Date of Patent: Nov. 15, 2022

(54) INDUCTION OF DIFFERENTIATION OF INDUCED PLURIPOTENT STEM CELLS INTO INTESTINAL EPITHELIAL CELLS

(71) Applicant: PUBLIC UNIVERSITY CORPORATION NAGOYA CITY UNIVERSITY, Nagoya (JP)

(72) Inventors: Takahiro Iwao, Nagoya (JP); Tomoki Kabeya, Nagoya (JP); Tamihide Matsunaga, Nagoya (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 976 days.

(21) Appl. No.: 16/083,226

(22) PCT Filed: Mar. 3, 2017

(86) PCT No.: PCT/JP2017/008616
§ 371 (c)(1),
(2) Date: Sep. 26, 2018

(87) PCT Pub. No.: WO2017/154795
PCT Pub. Date: Sep. 14, 2017

(65) Prior Publication Data
US 2019/0079076 A1 Mar. 14, 2019

(30) Foreign Application Priority Data
Mar. 8, 2016 (JP) ............................. JP2016-044088

(51) Int. Cl.
| C12N 5/00 | (2006.01) |
| G01N 33/50 | (2006.01) |
| C12N 5/071 | (2010.01) |
| C12N 5/16 | (2006.01) |
| A61L 27/00 | (2006.01) |
| C12N 5/074 | (2010.01) |
| A61K 35/38 | (2015.01) |

(52) U.S. Cl.
CPC .......... *G01N 33/5044* (2013.01); *A61L 27/00* (2013.01); *C12N 5/0679* (2013.01); *C12N 5/0696* (2013.01); *C12N 5/16* (2013.01); *G01N 33/5073* (2013.01); *A61K 35/38* (2013.01); *C12N 2501/01* (2013.01); *C12N 2501/11* (2013.01); *C12N 2501/115* (2013.01); *C12N 2501/15* (2013.01); *C12N 2501/727* (2013.01); *C12N 2506/45* (2013.01)

(58) Field of Classification Search
None
See application file for complete search history.

(56) References Cited

U.S. PATENT DOCUMENTS

| 2015/0201588 A1* | 7/2015 | Kamb ................ A01K 67/0271 800/9 |
| 2017/0292116 A1* | 10/2017 | Wells ........................ A61P 1/00 |

FOREIGN PATENT DOCUMENTS

| JP | 2008-206510 A | 9/2008 |
| JP | 2012-511935 A | 5/2012 |
| JP | 6296399 B | 3/2018 |
| WO | 2010/077955 A1 | 7/2010 |
| WO | 2014/132933 A1 | 9/2014 |

OTHER PUBLICATIONS

Nao Kodama et al., "Inhibition of mitogen-activated protein kinase kinase, DNA methyltransferase, and transforming growth factor—[beta] promotes differentiation of human induced pluripotent stem cells into enterocytes", Drug Metabolism and Pharmacokinetics, vol. 31, No. 3, Feb. 17, 2016, pp. 193-200. (cited in the Sep. 19, 2019 Search Report issued for EP17763135.5).
Maite Rocio Arana et al., "Coordinated induction of GST and MRP2 by cAMP in Caco-2 cells: Role of protein kinase A signaling pathway and toxicological relevance", Toxicology and Applied Pharmacology, Academic Press, Amsterdam, NL, vol. 287, No. 2, Jun. 3, 2015, pp. 178-190 (cited in the Sep. 19, 2019 Search Report issued for EP17763135.5).
Daisuke Sakano et al., "VMAT2 identified as a regulator of late-stage beta-cell differentiation", Nature Chemical Biology, vol. 10, No. 2, Feb. 1, 2014, pp. 141-148 and information sheets. (cited in the Sep. 19, 2019 Search Report issued for EP17763135.5).
Supplementary European Sheet dated Sep. 19, 2019, issued for the European patent application No. 17763135.5.
T. Ueda et al., "Generation of functional gut-like organ from mouse induced pluripotent stem cells," Biochemical and Biophysical Research Communication, 391, 2010, pp. 38-42. (discussed in the spec).
K. W. McCracken et al., "Generating human intestinal tissue from pluripotent stem cells in vitro," Nature Protocols, vol. 6, No. 12, 2011, pp. 1920-1928. (discussed in the spec).
J. R. Spence et al., "Directed differentiation of human pluripotent stem cells into intestinal tissue in vitro," Nature, Feb. 3, 2011, 470 (7332), pp. 1-12. (discussed in the spec).
S. Ogaki et al., "Wnt and Notch Signals Guide Embryonic Stem Cell Differentiation into the Intestinal Lineages," Stem Cells. 31, 2013, pp. 1086-1096. (discussed in the spec).

(Continued)

*Primary Examiner* — Marcia S Noble
(74) *Attorney, Agent, or Firm* — Locke Lord LLP

(57) ABSTRACT

An object of the present invention is to provide a novel method which enables convenient preparation of cells exhibiting functions close to that of intestinal epithelial cells of living bodies, and use of the method. The differentiation of induced pluripotent stem cells into intestinal epithelial cells is induced by step of differentiating induced pluripotent stem cells into endoderm-like cells; step of differentiating the endoderm-like cells obtained in step into intestinal stem cell-like cells; and step of differentiating the intestinal stem cell-like cells obtained in step into intestinal epithelial cell-like cells, wherein step includes culture in the presence of a MEK1 inhibitor, a DNA methyltransferase inhibitor, a TGF-β receptor inhibitor, and EGF and under the condition that cAMP is supplied to the cells.

13 Claims, 12 Drawing Sheets

(56) References Cited

OTHER PUBLICATIONS

T. Ozawa et al., "Generation of enterocyte-like cells from Human induced pluripotent stem cells for drug absorption and metabolism studies in human small intestine," Scientific Reports, 5, srep16479, Nov. 12, 2015, pp. 1-11. (discussed in the spec).

S. Ogaki et al., "A cost-effective system for differentiation of intestinal epithelium from human induced pluripotent stem cells," Scientific Reports, 5, srep17297, Nov. 30, 2015, pp. 1-11. (discussed in the spec).

T. Iwao et al., "Differentiation of Human Induced Pluripotent Stem Cells into Functional Enterocyte-like Cells Using a Simple Method," Drug Metab Pharmacokinet, 29(1), 2014, pp. 44-51. (discussed in the spec).

T. Iwao et al., "Generation of Enterocyte-Like Cells with Pharmacokinetic Functions from Human Induced Pluripotent Stem Cells Using Small-Molecule Compounds," Drug Metabolism and Disposition, vol. 43, Apr. 2015 pp. 603-610. (cited in the ISR).

International Search Report dated May 30, 2017, issued for PCT/JP2017/008616.

Office Action dated Jan. 19, 2021 issued in the corresponding Japanese patent application No. 2018-504455 with its English Machine Translation.

Sandro Pignata et al., "The Enterocyte-like Differentiation of the Caco-2 Tumor Cell Line Strongly Correlates with Responsiveness to cAMP and Activation of Kinase A Pathway," Cell Growth Differ., Sep. 1994, vol. 5, No. 9, pp. 967-973. (cited in the Jan. 19, 2021 Office Action issued for JP2018-504455).

Rocio Lopez-Posadas et al., "Tissue-nonspecific Alkaline Phosphatase Is Activated in Enterocytes by Oxidative Stress Via Changes in Glycosylation," Inflamm. Bowel. Dis., Feb. 2011, vol. 17, No. 2, pp. 543-556. (cited in the Jan. 19, 2021 Office Action issued for JP2018-504455.

Office Action dated Jun. 18, 2021, issued in the corresponding European patent application No. 17763135.5.

\* cited by examiner

INDUCTION OF DIFFERENTIATION OF INDUCED PLURIPOTENT STEM CELLS INTO INTESTINAL EPITHELIAL CELLS

TECHNICAL FIELD

The present invention relates to a method for inducing differentiation of induced pluripotent stem (iPS) cells into intestinal epithelial cells and use of the method. The present application claims priority based on Japanese Patent Application No. 2016-044088 filed on Mar. 8, 2016, the entire contents of which are incorporated herein by reference.

BACKGROUND ART

Due to the presence of many drug metabolizing enzymes and drug transporters in the small intestine, the small intestine, like the liver, is very important as an organ involved in the drug's first pass effect. Therefore, evaluating the membrane permeability and metabolism of drugs in the small intestine from early stages of pharmaceutical development is necessary for development of drugs with excellent pharmacokinetic properties. Currently, Caco-2 cells derived from human colon cancer are frequently used as a model system of the small intestine. However, the expression pattern of drug transporters in Caco-2 cells is different from that in the human small intestine. In addition, it is difficult to accurately evaluate the pharmacokinetics in the small intestine, because the expression of drug metabolizing enzymes and the enzyme induction are hardly observed in Caco-2 cells. Therefore, to comprehensively evaluate the drug metabolism and membrane permeability in the small intestine, it is desirable to use primary small intestinal epithelial cells, but the primary small intestinal epithelial cells are difficult to obtain.

Human induced pluripotent stem (iPS) cells were established in 2007 by Yamanaka et al. The human iPS cells are cells having pluripotency and almost infinite proliferative ability similar to those of the human embryonic stem (ES) cells established in 1998 by Thomson et al. Human iPS cells have less ethical problems than human ES cells and are expected as a stable cell source for pharmaceutical development.

In order to provide intestinal epithelial cells for use in drug absorption tests and the like, a method for selectively obtaining intestinal stem/progenitor cells from intestinal tract-derived cells has been reported (Patent Literature 1). In addition, a method for preparing and maintaining pluripotent cells using an ALK5 inhibitory factor has been proposed (Patent Literature 2).

CITATION LIST

Patent Literature

Patent Literature 1: Japanese Unexamined Patent Application Publication No. 2008-206510 A
Patent Literature 2: Japanese Translation of PCT International Application Publication No. 2012-511935 A
Patent Literature 3: PCT International Publication No. WO 2014/132933

Non-Patent Literature

Non-Patent Literature 1: Ueda T et al., Biochem Biophys Res Commun. 2010 Jan. 1; 391(1):38-42.
Non-Patent Literature 2: McCracken K W et al., Nat Protoc. 2011 Nov. 10; 6(12): 1920-8
Non-Patent Literature 3: Spence J R, Nature. 2011 Feb. 3; 470(7332): 105-109.
Non-Patent Literature 4: Ogaki S et al., Stem Cells. 2013 June; 31(6): 1086-1096.
Non-Patent Literature 5: Ozawa T et al., Sci Rep. 2015 Nov. 12; 5: 16479.
Non-Patent Literature 6: Ogaki S et al., Sci Rep. 2015 Nov. 30; 5: 17297.
Non-Patent Literature 7: Iwao T et al., Drug Metab Pharmacokinet, 29(1), 44-51 (2014).
Non-Patent Literature 8: Iwao T et al., Drug Metab Dispos, 43(6), 603-610 (2015).

SUMMARY OF INVENTION

Technical Problem

Currently, there are few reports on differentiation of iPS cells into the intestinal tract. It has been reported that embryoids were formed from mouse iPS cells to prepare intestinal tract-like tissues (Non-Patent Literature 1) and that intestinal tract-like tissues were prepared from human iPS cells by three-dimensional culture (Non-Patent Literatures 2 and 3). However, the differentiation inducing methods in these reports are complicated and, additionally, provide insufficient differentiation efficiency, and no pharmacokinetic analysis has been made in detail. Further, the differentiation inducing method induces differentiation by using very expensive growth factors and cytokines in large amounts, which is not suitable for practical use. Thereafter, successful differentiation of human pluripotent stem cells (ES cells or iPS cells) into intestinal tract cells has been reported (Non-Patent Literatures 4, 5, and 6), but the pharmacokinetic functions have not been made clear. The present inventors also have studied differentiation of human iPS cells into intestinal epithelial cells and reported that the intestinal epithelial cell-like cells prepared have various pharmacokinetic functions (Patent Literature 3 and Non-Patent Literatures 7 and 8). In addition, the present inventors have found small molecule compounds useful for promoting differentiation of human iPS cells into intestinal epithelial cells and acquiring functions (Patent Literature 3 and Non-Patent Literature 8).

As described above, vigorous studies have been conducted by many researchers and certain results have been obtained. However, the needs for preparing functional intestinal epithelial cells that can be used for pharmacokinetic assays, toxicity tests, and the like in vitro are still high. Therefore, an object of the present invention is to provide a novel method which enables convenient preparation of cells (intestinal epithelial cell-like cells) exhibiting a function close to that of intestinal epithelial cells of living bodies, and use of the methods.

Solution to Problem

For the above-mentioned object, the present inventors have focused attention on small molecule compounds having an action different from those of the previously-reported small molecule compounds (Patent Literature 3) and examined, in detail, its action/effect on the differentiation of iPS cells into intestinal epithelial cells. The present inventors have also studied, in detail, the pharmacokinetic function of the intestinal epithelial cell-like cells obtained by inducing differentiation using the small molecule compounds confirmed to be useful.

As a result of the study, cAMP has been found to be important as an inducing factor at the time of inducing differentiation of the intestinal stem cell-like cells obtained from iPS cells via endoderm-like cells into intestinal epithelial cell-like cells. Specifically, it has been revealed that, in addition to the presence of the previously-reported small molecule compounds (a MEK1 inhibitor, a DNA methyltransferase inhibitor, and a TGF-β receptor inhibitor) in a medium, culturing the cells under the condition that cAMP is supplied to the cells and suppressing a decrease in intracellular cAMP concentration by using a cAMP-degrading enzyme inhibitor are effective for inducing differentiation into intestinal epithelia, in particular, acquiring functions as intestinal epithelial cells. In addition, there has been provided a useful finding on the relationship between the timing of addition of the small molecule compounds to be used and the effect.

The intestinal epithelial cell-like cells prepared under the culture conditions found at the end of the study highly express an intestinal epithelium-specific enzyme (drug metabolizing enzyme) and exhibit good induction of expression of a drug metabolizing enzyme (CYP3A4) mediated via a vitamin D receptor. Also, the cells have the transport functions of the uptake and efflux transporters.

As described above, the present inventors have found novel small molecule compounds that are useful for promoting differentiation and acquiring functions, and succeeded in preparing more functional intestinal epithelial cell-like cells. The following inventions are mainly based on the above results and observations.

[1] A method for inducing differentiation of induced pluripotent stem cells into intestinal epithelial cells, comprising:
step (1) of differentiating induced pluripotent stem cells into endoderm-like cells; step (2) of differentiating the endoderm-like cells obtained in step (1) into intestinal stem cell-like cells; and
step (3) of differentiating the intestinal stem cell-like cells obtained in step (2) into intestinal epithelial cell-like cells, wherein step (3) includes culture in the presence of a MEK1 inhibitor, a DNA methyltransferase inhibitor, a TGF-β receptor inhibitor, and EGF and under the condition that cAMP is supplied to the cells.

[2] The method according to [1], wherein the period of the culture in step (3) is from 7 days to 40 days.

[3] The method according to [1], wherein step (3) comprises any one of:
culture step A: including (a-1) culture in the presence of a MEK1 inhibitor, a DNA methyltransferase inhibitor, a TGF-β receptor inhibitor, and EGF, followed by (a-2) culture in the presence of a MEK1 inhibitor, a DNA methyltransferase inhibitor, a TGF-β receptor inhibitor, and EGF and under the condition that cAMP is supplied to the cells;
culture step B: including (b-1) culture in the presence of a MEK1 inhibitor, a DNA methyltransferase inhibitor, a TGF-β receptor inhibitor, and EGF and under the condition that cAMP is supplied to the cells, followed by (b-2) culture in the presence of a MEK1 inhibitor, a DNA methyltransferase inhibitor, a TGF-β receptor inhibitor, EGF, and a cAMP-degrading enzyme inhibitor; and
culture step C: including (c-1) culture in the presence of a MEK1 inhibitor, a DNA methyltransferase inhibitor, a TGF-β receptor inhibitor, and EGF and under the condition that cAMP is supplied to the cells.

[4] The method according to [3],
wherein the period of culture (a-1) is 1 day to 5 days, and the period of culture (a-2) is 3 days to 15 days;
wherein the period of culture (b-1) is 3 days to 15 days, and the period of culture (b-2) is 3 days to 15 days; and
wherein the period of culture (c-1) is 3 days to 15 days.

[5] The method according to [3] or [4], wherein culture (a-2), culture (b-1), and culture (c-1) are carried out under the condition that the cAMP-degrading enzyme inhibitor exists in addition to the MEK1 inhibitor, DNA methyltransferase inhibitor, TGF-β receptor inhibitor, and EGF.

[6] The method according to any one of [2] to [5],
wherein culture step A includes (a-3) culture in the presence of a MEK1 inhibitor, a DNA methyltransferase inhibitor, a TGF-β receptor inhibitor, and EGF, following culture (a-2);
wherein culture step B includes (b-3) culture in the presence of a MEK1 inhibitor, a DNA methyltransferase inhibitor, a TGF-β receptor inhibitor, and EGF, following culture (b-2); and
wherein culture step C includes (c-2) culture in the presence of a MEK1 inhibitor, a DNA methyltransferase inhibitor, a TGF-β receptor inhibitor, and EGF, following culture (c-1).

[7] The method according to [6], wherein the periods of culture (a-3), culture (b-3) and culture (c-2) are each 1 day to 10 days.

[8] The method according to any one of [1] to [7], wherein the condition that cAMP is supplied to the cells is the presence of 8-Br-cAMP in a medium.

[9] The method according to any one of [1] to [8], wherein the cAMP-degrading enzyme inhibitor is IBMX.

[10] The method according to any one of [1] to [9], wherein the MEK1 inhibitor is PD98059, the DNA methyltransferase inhibitor is 5-aza-2'-deoxycytidine, and the TGF-β receptor inhibitor is A-83-01.

[11] The method according to any one of [1] to [10], wherein activin A is used as a differentiation inducing factor in step (1).

[12] The method according to any one of [1] to [11], wherein FGF2 is used as a differentiation inducing factor in step (2).

[13] The method according to any one of [1] to [12], wherein the induced pluripotent stem cells are human induced pluripotent stem cells.

[14] An intestinal epithelial cell-like cell obtained by the method according to any one of [1] to [13].

[15] A method for evaluating in vivo drug disposition or toxicity of a test substance using the intestinal epithelial cell-like cell according to [14].

[16] The method according to [15], wherein the in vivo drug disposition is metabolism, absorption, excretion, drug interaction, induction of a drug metabolizing enzyme, or induction of a drug transporter.

[17] The method according to [15] or [16] comprising:
step (i) of preparing a cell layers composed of the intestinal epithelial cell-like cell according to [14];
step (ii) of bringing a test substance into contact with the cell layers; and
step (iii) of quantifying the test substance having permeated the cell layers and evaluating the absorbability or membrane permeability, drug interaction, induction of a drug metabolizing enzyme, induction of a drug transporter, or toxicity of the test substance.

[18] The method according to [15] or [16] comprising:
step (I) of bringing the test substance into contact with the intestinal epithelial cell-like cell according to [14]; and step (II) of measuring and evaluating the metabolism or absorption, drug interaction, induction of a drug metabolizing enzyme, induction of a drug transporter, or toxicity of the test substance.

[19] A method for evaluating a digestive tract mucosa damaging action of a test substance, comprising:
step (a) of bringing a test substance into contact with the intestinal epithelial cell-like cell according to [14]; and
step (b) of detecting the expression of mucin 2 in the intestinal epithelial cell-like cell and determining the digestive tract mucosa damaging action of the test substance based on the detection result, wherein a decrease in expression of mucin 2 is indicative for a digestive tract mucosa damaging action of the test substance.

[20] A method for evaluating a digestive tract mucosa protecting action of a test substance, comprising:
step (A) of bringing a test substance into contact with the intestinal epithelial cell-like cell according to [14]; and
step (B) of detecting the expression of mucin 2 in the intestinal epithelial cell-like cell and determining the digestive tract mucosa protecting action of the test substance based on the detection result, wherein a increase in expression of mucin 2 by the substance is indicative for a digestive tract mucosa protecting action of the test substance.

[21] A cell preparation comprising the intestinal epithelial cell-like cell according to [14].

Figure 1:
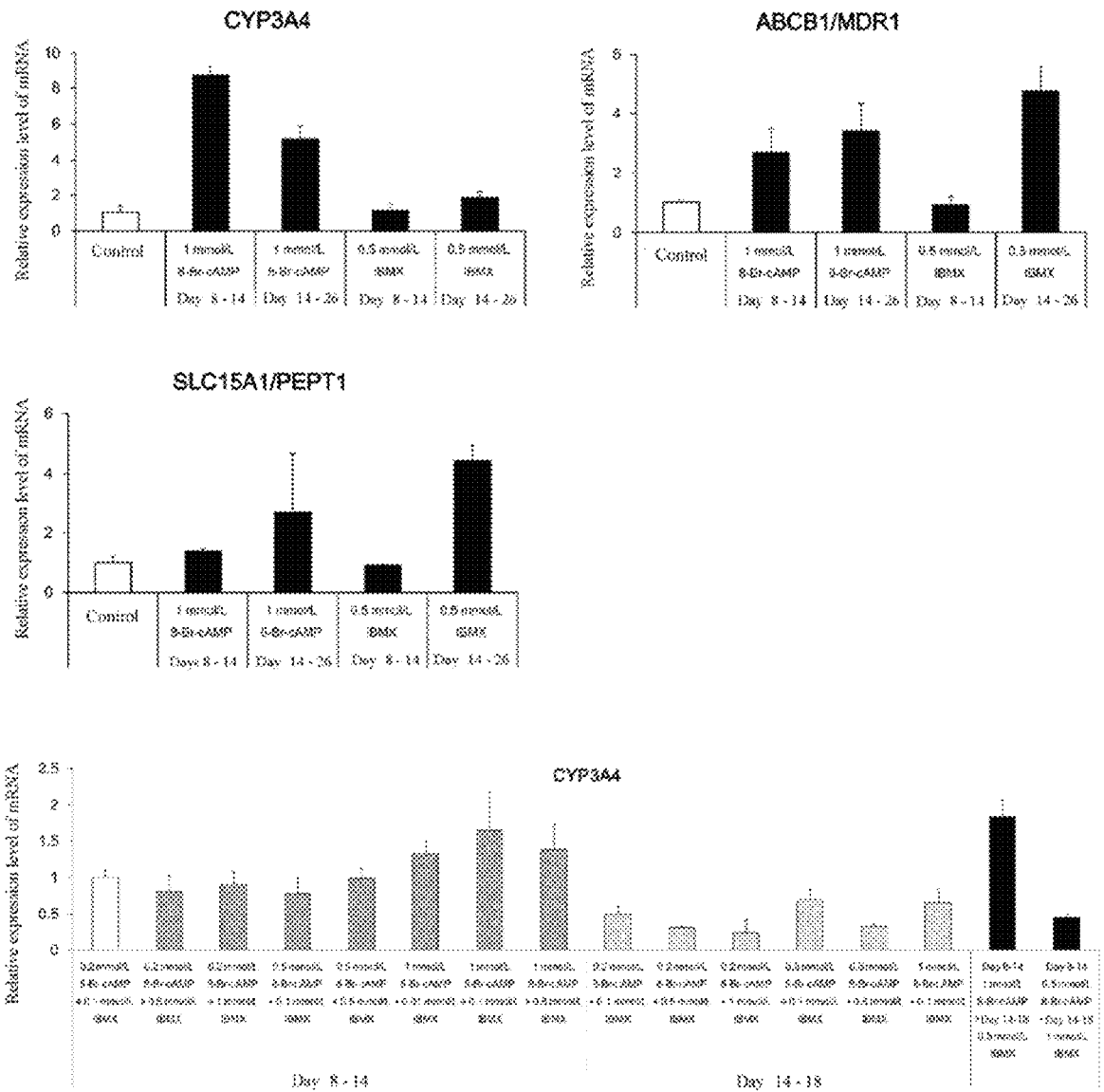
FIG. 1 shows effects of 8-Br-cAMP and IBMX on differentiation of human iPS cells into intestinal epithelial cells. Expressed by average value±S.D. (n=3). Control is a group without addition of 8-Br-cAMP or IBMX.

Control: Control (cells cultured in a medium to which neither a substance exhibiting a mucosa damaging action nor a substance having a mucosa protecting action was added).

Meloxicam-50: Cells cultured in a medium to which meloxicam was added in a concentration of 50 µM.

Meloxicam-200: Cells cultured in a medium to which meloxicam was added in a concentration of 200 µM.

Indomethacin-75: Cells cultured in a medium to which indomethacin was added in a concentration of 75 µM.

Indomethacin-300: Cells cultured in a medium to which indomethacin was added in a concentration of 300 µM.

Ketoprofen-200: Cells cultured in a medium to which ketoprofen was added in a concentration of 200 µM.

Ketoprofen-800: Cells cultured in a medium to which ketoprofen was added in a concentration of 800 µM.

Irsogladine-10: Cells cultured in a medium to which irsogladine was added in a concentration of 10 µM.

Irsogladine-40: Cells cultured in a medium to which irsogladine was added in a concentration of 40 µM.

Rebamipide-50: Cells cultured in a medium to which rebamipide was added in a concentration of 50 µM.

Rebamipide-100: Cells cultured in a medium to which rebamipide was added in a concentration of 100 µM.

Rebamipide-250: Cells cultured in a medium to which rebamipide was added in a concentration of 250 µM.

Rebamipide-1000: Cells cultured in a medium to which rebamipide was added in a concentration of 1000 µM.

SI: Commercially available human small intestine cells.
Caco-2: Cells derived from human colon cancer.

DESCRIPTION OF EMBODIMENTS

The present invention relates to a method for inducing differentiation of induced pluripotent stem cells (iPS cells) along the intestinal epithelial cell lineage (hereinafter referred to also as "differentiation inducing method of the present invention"). According to the present invention, cells exhibiting properties similar to those of intestinal epithelial cells constituting the intestinal tissue of a living body, that is, intestinal epithelial cell-like cells are obtained.

The "induced pluripotent stem cell (iPS cell)" is a cell having pluripotency (multipotency) and proliferative ability, which is prepared by reprogramming a somatic cell by introduction of an initialization factor or the like. The induced pluripotent stem cell exhibits properties similar to those of an ES cell. The somatic cell used in the preparation of an iPS cell is not particularly limited, and may be a differentiated somatic cell or an undifferentiated stem cell. Also, its origin is not particularly limited, but somatic cells of mammals (for example, primates such as humans or chimpanzees, and rodents such as mice or rats), particularly preferably human somatic cells are used. iPS cells can be prepared by various methods reported so far. The application of iPS cell preparation methods which will be developed in the future is also necessarily contemplated.

The most fundamental technique of iPS cell preparation methods is to introduce four factors Oct3/4, Sox2, Klf4, and c-Myc, which are transcription factors, into cells using a virus (Takahashi K, Yamanaka S: Cell 126 (4), 663-676, 2006; Takahashi, K, et al.: Cell 131 (5), 861-72, 2007). The establishment of human iPS cells by introduction of four factors Oct4, Sox2, Lin28, and Nonog has been reported (Yu J, et al.: Science 318 (5858), 1917-1920, 2007). The establishment of iPS cells by introduction of the three factors other than c-Myc (Nakagawa M, et al.: Nat. Biotechnol. 26 (1), 101-106, 2008), two factors Oct3/4 and Klf4 (Kim J B, et al.: Nature 454 (7204), 646-650, 2008), or only Oct3/4 (Kim J B, et al.: Cell 136 (3), 411-419, 2009) has also been reported. Also, techniques of introducing a protein, which is an expression product of a gene, into cells (Zhou H, Wu S, Joo J Y, et al.: Cell Stem Cell 4, 381-384, 2009; Kim D, Kim C H, Moon J I, et al.: Cell Stem Cell 4, 472-476, 2009) have also been reported. On the other hand, it has been reported to be possible to improve the preparation efficiency and reduce the factors to be introduced, by using, for example, an inhibitor BIX-01294 against histone methyltransferase G9a, a histone deacetylase inhibitor valproic acid (VPA) or BayK8644 (Huangfu D, et al.: Nat. Biotechnol. 26 (7), 795-797, 2008; Huangfu D, et al.: Nat. Biotechnol. 26 (11), 1269-1275, 2008; Silva J, et al.: PLoS. Biol. 6 (10), e 253, 2008). Studies have also been advanced on gene transfer methods, and techniques utilizing not only retroviruses, but also lentiviruses (Yu J, et al.: Science 318 (5858), 1917-1920, 2007), adenoviruses (Stadtfeld M, et al.: Science 322 (5903), 945-949, 2008), plasmids (Okita K, et al.: Science 322 (5903), 949-953, 2008), transposon vectors (Woltjen K, Michael I P, Mohseni P, et al.: Nature 458, 766-770, 2009; Kaji K, Norrby K, Pac a A, et al.: Nature 458, 771-775, 2009; Yusa K, Rad R, Takeda J, et al.: Nat Methods 6, 363-369, 2009), or episomal vectors (Yu J, Hu K, Smuga-Otto K, Tian S, et al.: Science 324, 797-801, 2009) for gene transfer have been developed.

Cells in which transformation into iPS cells, i.e., initialization (reprogramming) has occurred can be selected by using, as an index, the expression of pluripotent stem cell markers (undifferentiation markers) such as Fbxo15, Nanog, Oct/4, Fgf-4, Esg-1, and Cript. The selected cells are collected as iPS cells.

iPS cells can also be provided, for example, from the National University Corporation Kyoto University or the Independent Administrative Institution RIKEN BioResource Center.

As used herein, the phrase "inducing differentiation" refers to working on differentiation along a specific cell lineage. In the present invention, iPS cells are induced to differentiate into intestinal epithelial cells. The differentiation inducing method of the present invention includes, roughly, three induction steps, that is, a step (step (1)) of differentiating iPS cells into endoderm-like cells, a step (step (2)) of differentiating the obtained endoderm-like cells into intestinal stem cell-like cells, and a step (step (3)) of differentiating the obtained intestinal stem cell-like cells into intestinal epithelial cell-like cells. Each of the steps will be described in detail below.

<Step (1) Differentiation into Endoderm-Like Cells>

In this step, iPS cells are cultured and differentiated into endoderm-like cells. In other words, iPS cells are cultured under the conditions for inducing differentiation into endoderm-like cells. As long as iPS cells differentiate into endoderm-like cells, the culture conditions are not particularly limited. For example, iPS cells are cultured in a medium to which activin A has been added according to a conventional method. In this case, the concentration of activin A in the medium is, for example, 10 ng/mL to 200 ng/mL, preferably 20 ng/mL to 150 ng/mL. It is preferable to add serum or serum replacement (such as Knockout serum replacement (KSR)) to the medium from the viewpoint of cell growth rate, maintenance, and the like. The serum is not limited to fetal bovine serum, and human serum, sheep serum, etc. can also be used. The amount of the serum or serum replacement to be added is, for example, 0.1% (v/v) to 10% (v/v).

Inhibitors of the Wnt/β-catenin signaling pathway (hexachlorophene, quercetin, Wnt ligand Wnt3a, etc.) may be added to the medium to promote differentiation into endoderm-like cells.

In one preferred embodiment, two-stage culture is carried out as step (1). The culture at the first stage is carried out in a medium to which a relatively low concentration of serum (for example, 0.1% (v/v) to 1% (v/v)) has been added, and the subsequent culture at the second stage is carried out in a medium having a serum concentration higher than that of the medium used at the first stage (serum concentration is, for example, 1% (v/v) to 10% (v/v)). Adopting the two-stage culture is preferable in that growth of undifferentiated cells is suppressed by the culture at the first stage and that differentiated cells are proliferated by the subsequent second stage.

The period of step (1) (culture period) is, for example, 1 day to 10 days, preferably 2 days to 7 days. When adopting the two-stage culture as step (1), the first-stage culture period is set to, for example, 1 day to 7 days, preferably 2 days to 5 days, and the second-stage culture period is set to, for example, 1 day to 6 days, preferably 1 day to 4 days.

<Step (2) Differentiation into Intestinal Stem Cell-Like Cells>

In this step, the endoderm-like cells obtained in step (1) are cultured and differentiated into intestinal stem cell-like cells. In other words, endodermal-like cells are cultured under the conditions for inducing differentiation into intestinal stem cell-like cells. As long as the endoderm-like cells differentiate into intestinal stem cell-like cells, the culture conditions are not particularly limited. Preferably, culture is carried out in the presence of FGF2 (fibroblast growth factor 2) based on the experimental results shown in Examples described later. Preferably, human FGF2 (e.g., human recombinant FGF2) is used.

Typically, the cell population obtained through step (1) or a part thereof is subjected to step (2) without sorting. On the other hand, step (2) may be carried out after sorting endoderm-like cells from the cell population obtained through step (1). Sorting of endoderm-like cells may be performed, for example, with a flow cytometer (cell sorter) with the cell surface marker being used as an index.

The phrase "in the presence of FGF2" is synonymous with the condition that FGF2 has been added to the medium. Therefore, in order to carry out culture in the presence of FGF2, a medium to which FGF2 has been added may be used. An example of the concentration of FGF2 to be added is 100 ng/mL to 500 ng/mL.

The period of step (2) (culture period) is, for example, 2 days to 10 days, preferably 3 days to 7 days. If the culture period is too short, the expected effects (rise in differentiation efficiency and promotion of acquisition of functions as intestinal stem cells) cannot be obtained sufficiently. On the other hand, if the culture period is too long, the differentiation efficiency is lowered.

Differentiation into intestinal stem cell-like cells can be determined or evaluated, for example, using the expression of an intestinal stem cell marker as an index. Examples of the intestinal stem cell marker include leucine-rich repeat containing G-protein-coupled receptor 5 (LGR5) and Ephrin B2 receptor (EphB2).

<Step (3) Differentiation into Intestinal Epithelial Cell-Like Cells>

In this step, culture is carried out in the presence of a MEK1 inhibitor, a DNA methyltransferase inhibitor, a TGF-β receptor inhibitor, and EGF (hereinafter, this condition is referred to as "first condition") and under the condition that cAMP is supplied to the cells (hereinafter, this condition is referred to as "second condition") to differentiate the intestinal stem cell-like cells obtained in step (2) into intestinal epithelial cell-like cells. Typically, the cell population obtained through step (2) or a part thereof is subjected to step (3) without sorting. On the other hand, step (3) may be carried out after sorting intestinal stem cell-like cells from the cell population obtained through step (2). Sorting of intestinal stem cell-like cells may be performed, for example, with a flow cytometer (cell sorter) with the cell surface marker being used as an index.

The "first condition", that is, "in the presence of a MEK1 inhibitor, a DNA methyltransferase inhibitor, a TGF-β receptor inhibitor and EGF" is synonymous with the condition that these compounds have been added to the medium. Therefore, in order to satisfy the first condition, a medium to which these compounds have been added may be used.

Examples of the MEK1 inhibitor can include PD98059, PD184352, PD184161, PD0325901, U0126, MEK inhibitor I, MEK inhibitor II, MEK1/2 inhibitor II, and SL327. Likewise, 5-aza-2'-deoxycytidine, 5-azacytidine, RG 108, and zebularine can be listed as the DNA methyltransferase inhibitors. Considering that A-83-01 used in Examples described later shows inhibitory activity against TGF-β receptors ALK4, ALK5, and ALK7, a TGF-β receptor inhibitor that exhibits inhibitory activity against one or more of the TGF-β receptors ALK 4, ALK 5, and ALK 7 is preferably used. For example, A-83-01, SB431542, SB505124, SB525334, D4476, ALK5 inhibitor, LY2157299, LY364947, G 788388, and RepSox satisfy this condition.

An example of the concentration of the MEK1 inhibitor to be added (in the case of PD98059) is 4 µM to 100 µM, preferably 10 to 40 µM. Similarly, an example of the concentration of the DNA methyltransferase inhibitor to be added (in the case of 5-aza-2'-deoxycytidine) is 1 µM to 25 µM, preferably 2.5 µM to 10 µM, and an example of the concentration of the TGF-β receptor inhibitor to be added (in the case of A-83-01) is 0.1 µM to 2.5 µM, preferably 0.2 µM to 1 µM. With respect to the addition concentration when compounds different from the exemplified compounds, i.e., PD98059, 5-aza-2'-deoxycytidine, and A-83-01, are used, those skilled in the art can set the concentrations according to the above concentration ranges in view of the differences (in particular, difference in activity) between the properties of the compounds to be used and the properties of the exemplified compounds (PD98059, 5-aza-2'-deoxycytidine, and A-83-01). The appropriateness of the set concentration ranges can be confirmed by preliminary experiments according to Examples described later.

The "second condition", that is, "the condition that cAMP is supplied to the cell" is synonymous with the condition that there exists a compound which can be incorporated into the cells and which, when incorporated into the cells, acts as cAMP. Therefore, in order to satisfy the second condition, for example, a medium to which a cAMP derivative that can be incorporated into the cells has been added may be used. As the cAMP derivative, a PKA activator (8-Br-cAMP (8-Bromoadenosine-3',5'-cyclic monophosphate sodium salt, CAS Number: 76939-46-3), 6-Bnz-cAMP (N6-Benzoyladenosine-3',5'-cyclic monophosphate sodium salt, CAS Number: 1135306-29-4), cAMPS-Rp ((R)-Adenosine, cyclic 3',5'-(hydrogenphosphorothioate) triethylammonium salt, CAS Number: 151837-09-1), cAMPS-Sp((S)-Adenosine, cyclic 3',5'-(hydrogenphosphorothioate) triethylammonium salt, CAS Number: 93602-66-5), Dibutyryl-cAMP (N6,O2'-Dibutyryl adenosine 3',5'-cyclic monophosphate sodium salt salt, CAS Number: 16980-89-5), 8-Cl-cAMP (8-Chloroadenosine-3',5'-cyclic monophosphate salt, CAS Number: 124705-03-9), Epac activator (Rp-8-Br-cAMPS (8-Bromoadenosine 3',5'-cyclic Monophosphothioate, Rp-Isomer. sodium salt, CAS Number: 129735-00-8), 8-CPT-cAMP (8-(4-Chlorophenylthio)adenosine 3',5'-cyclic monophosphate, CAS Number: 93882-12-3), 8-pCPT-2'-O-Me-cAMP (8-(4-Chlorophenylthio)-2'-O-methyladenosine 3',5'-cyclic monophosphate monosodium, CAS Number: 634207-53-7), etc.) can be adopted. An example of the concentration of the cAMP derivative to be added (in the case of 8-Br-cAMP) is 0.1 mM to 10 mM, preferably 0.2 mM to 5 mM, more preferably 0.5 mM to 2 mM. Regarding the addition concentration when a compound different from the exemplified compound, i.e., 8-Br-cAMP, is used, those skilled in the art can set the concentration according to the above concentration range in view of the differences (in particular, difference in activity) between the properties of the compound to be used and the properties of the exemplified compound (8-Br-cAMP). The appropriateness of the set concentration ranges can be confirmed by preliminary experiments according to Examples described later.

The period of step (3) (culture period) is, for example, 7 days to 40 days, preferably 10 days to 30 days. If the culture period is too short, the expected effects (rise in differentiation efficiency and promotion of acquisition of functions as intestinal epithelial cells) cannot be obtained sufficiently. On the other hand, if the culture period is too long, the differentiation efficiency is lowered.

Differentiation into intestinal epithelial cell-like cells can be determined or evaluated, for example, using the expression of an intestinal epithelial cell marker, uptake of a peptide, or induction of expression of a drug metabolizing enzyme via a vitamin D receptor as an index. Examples of the intestinal epithelial cell marker include ATP binding cassette transporter B1/multidrug resistant protein 1 (ABCB1/MDR1), ATP binding cassette transporter G2/breast cancer resistant protein (ABCG2/BCRP), cytochrome P450 3A4 (CYP3A4), pregnane X receptor (PXR), SLC (solute carrier) family member 15A1/peptide transporter 1 (SLC15A1/PEPT1), SLC (solute carrier) organic anion transporter 2B1 (SLCO2B1/OATP2B1), sucrase-isomaltase, uridine diphosphate-glucuronosyl transferase 1A1 (UGT1A1), uridine diphosphate-glucuronosyl transferase 1A4 (UGT1A4), and villin 1 (Villin 1). Among these, particularly effective markers are: sucrase-isomaltase and villin 1 which are highly specific to the intestinal epithelium, CYP3A4 which is a major drug metabolizing enzyme in the small intestine, SLC15A1/PEPT1 involved in absorption of peptides in the small intestine, and SLCO2B1/OATP2B1 which is involved in absorption of organic anions in the small intestine.

If it is intended to obtain a cell population containing only a target cell (intestinal epithelial cell-like cell) or a cell population containing the targeted cell at a high ratio (high purity), a cell surface marker characteristic of the target cell may be used as an index to sort and fractionate cell populations after culture.

Preferably, any one of the following culture steps A to C is carried out as step (3).

<Culture Step A>

In culture step A, (a-1) culture in the presence of a MEK1 inhibitor, a DNA methyltransferase inhibitor, a TGF-β receptor inhibitor, and EGF is followed by (a-2) culture in the presence of a MEK1 inhibitor, a DNA methyltransferase inhibitor, a TGF-β receptor inhibitor and EGF and under the condition that cAMP is supplied to the cells. That is, two-step culture varying depending on the presence or absence of the condition that cAMP is supplied to the cells is carried out. In this way, the effects of promotion of differentiation into intestinal epithelial cells, maturation, and acquisition of functions can be obtained. The period of culture (a-1) is, for example, 1 day to 5 days. Similarly, the period of culture (a-2) is, for example, 3 days to 15 days. For the matters not specifically explained (compounds usable for each culture, concentration of each compound to be added, etc.), the corresponding explanations given above are quoted.

(a-2) culture may be carried out under the condition that a cAMP-degrading enzyme inhibitor is also present in addition to the MEK1 inhibitor, DNA methyltransferase inhibitor, TGF-β receptor inhibitor, and EGF. When this condition is adopted, it can be expected that the decrease in intracellular cAMP concentration is suppressed by inhibition of decomposition of cAMP, and that the induction of differentiation into intestinal epithelia, in particular, acquisition of functions as intestinal epithelial cells is promoted. That is, this condition is advantageous in preparation of more functional intestinal epithelial cell-like cells. Examples of the cAMP-degrading enzyme inhibitor can include IBMX (3-isobutyl-1-methylxanthine) (MIX), Theophylline, Papaverine, Pentoxifylline (Trental), KS-505, 8-Methoxymethyl-IBMX, Vinpocetine (TCV-3B), EHNA, Trequinsin (HL-725), Lixazinone (RS-82856), (LY-186126), Cilostamide (OPC3689), Bemoradan (RWJ-22867), Anergrelide (BL4162A), Indolidan (LY195115), Cilostazol (OPC-13013), Milrinone (WIN47203), Siguazodan (SKF-94836), 5-Methyl-imazodan (CI 930), SKF-95654, Pirilobendan (UD-CG 115 BS), Enoximone (MDL 17043), Imazodan (CL 914), SKF-94120, Vesnarinone (OPC 8212), Rolipram (Ro-20-1724), (ZK-62711), Denbufyll'ine, Zaprinast (M&B-22, 948), Dipyridamole, Zaprinast (M&B-22, 948), Dipyridamole, Zardaverine, AH-21-132, and Sulmazol (AR-L 115 BS). An example of the concentration of the cAMP-degrading enzyme inhibitor (in the case of IBMX) to be added is 0.05 mM to 5 mM, preferably 0.1 mM to 3 mM, more preferably 0.2 mM to 1 mM. With respect to the addition concentration when a compound different from the exemplified compound, i.e., IBMX is used, those skilled in the art can set according to the above concentration range in view of the differences (in particular, difference in activity) between the properties of the compound to be used and the properties of the exemplified compound (IBMX). The appropriateness of the set concentration ranges can be confirmed by preliminary experiments according to Examples described later.

Culture in the presence of a MEK1 inhibitor, a DNA methyltransferase inhibitor, a TGF-β receptor inhibitor and EGF (culture (a-3)) may be carried out after culture (a-2). The period of this culture is, for example, 1 day to 10 days. This culture provides the effects of promotion of differentiation into intestinal epithelial cells, maturation, and acquisition of functions.

<Culture Step B>

In culture step B, (b-1) culture in the presence of a MEK 1 inhibitor, a DNA methyltransferase inhibitor, a TGF β receptor inhibitor, and EGF and under the condition that cAMP is supplied to the cells is followed by (b-2) culture in the presence of a MEK1 inhibitor, a DNA methyltransferase inhibitor, a TGF-β receptor inhibitor, EGF, and a cAMP-degrading enzyme inhibitor. Thus, when culture under the condition that cAMP is supplied to the cells is followed by culture under the condition that the cAMP-degrading enzyme inhibitor is present, the effects of promotion of differentiation into intestinal epithelial cells, maturation, and acquisition of functions can be obtained. The period of culture (b-1) is, for example, 3 days to 15 days. Similarly, the period of culture (b-2) is, for example, 3 days to 15 days. For the matters not specifically explained (compounds usable for each culture, concentration of each compound to be added, etc.), the corresponding explanations given above are quoted.

Culture (b-1) may be carried out under the conditions that a cAMP-degrading enzyme inhibitor is present in addition to the MEK1 inhibitor, DNA methyltransferase inhibitor, TGF-β receptor inhibitor, and EGF. When this condition is adopted, it can be expected that the decrease in intracellular cAMP concentration is suppressed from the early stage, and induction of differentiation into intestinal epithelia, in particular, acquisition of functions as intestinal epithelial cells is promoted. That is, the condition is advantageous in efficient preparation of more functional intestinal epithelial cell-like cells.

Culture in the presence of a MEK1 inhibitor, a DNA methyltransferase inhibitor, a TGF-β receptor inhibitor, and EGF (culture (b-3)) may be carried out after culture (b-2). The period of this culture is, for example, 1 day to 10 days. This culture provides the effects of promotion of differentiation into intestinal epithelial cells, maturation, and acquisition of functions.

<Culture Step C>

In culture step C, (c-1) culture in the presence of a MEK1 inhibitor, a DNA methyltransferase inhibitor, a TGF-β receptor inhibitor, and EGF and under the condition that cAMP is supplied to the cells is carried out. The period of culture (c-1) is, for example, 3 days to 15 days. For the matters not specifically explained (compounds usable for each culture, concentration of each compound to be added, etc.), the corresponding explanations given above are quoted.

Culture (c-1) may be carried out under the condition that a cAMP-degrading enzyme inhibitor is present in addition to the MEK1 inhibitor, DNA methyltransferase inhibitor, TGF-β receptor inhibitor, and EGF (the condition that cAMP is supplied to cells is also used together). The use of this condition makes it possible to suppress the decrease in intracellular cAMP concentration while supplying cAMP to the cells. Therefore, this condition serves as an effective condition for maintaining intracellular cAMP at a high level, and it can be expected that efficient induction of differentiation into intestinal epithelial cells is promoted.

Culture in the presence of a MEK1 inhibitor, a DNA methyltransferase inhibitor, a TGF-β receptor inhibitor, and EGF (culture (c-2)) may be carried out after culture (c-1). The period of this culture is, for example, 1 day to 10 days. This culture provides the effects of promotion of differentiation into intestinal epithelial cells, maturation, and acquisition of functions.

In each of the steps (steps (1), (2), and (3) and culture steps A, B, and C constituting step (3)) constituting the present invention, subculture may be carried out halfway. For example, when the cells become confluent or subconfluent, part of the cells are collected and transferred to another culture vessel, and culture is continued. It is preferable to set the cell density to be low in order to promote differentiation. For example, cells are preferably seeded at a cell density of about $1\times10^4$ cells/cm$^2$ to about $1\times10^6$ cells/cm$^2$.

At the time of cell collection accompanied by medium exchange, subculture, etc., the cells are preferably treated with a ROCK (Rho-associated coiled-coil forming kinase/Rho binding kinase) inhibitor such as Y-27632 in advance in order to suppress cell death.

Other culture conditions (culture temperature and the like) in each of the steps constituting the present invention may be conditions generally adopted in culture of animal cells. Specifically, the cells may be cultured in an environment of, for example, 37° C. and 5% $CO_2$. In addition, as a basic medium, an Iscove's modified Dulbecco's medium (IMDM) (for example, GIBCO), a Ham's F12 medium (HamF 12) (SIGMA, Gibco, etc.), a Dulbecco's modified Eagle's medium (D-MEM) (Nacalai tesque, Sigma, Gibco, etc.), a Glasgow basic medium (for example, Gibco), a RPMI 1640 medium, and the like can be used. Two or more kinds of basic media may be used in combination. In steps (2) and (3) and culture steps A, B, and C constituting step (3), a basic medium suitable for culturing epithelial cells (a mixed medium of D-MEM and Ham F12, D-MEM, etc.) is preferably used. Examples of components that can be added to the medium can include bovine serum albumin (BSA), antibiotics, 2-mercaptoethanol, PVA, nonessential amino acids (NEAA), insulin, transferrin, and selenium. Typically, the cells are cultured two-dimensionally using a culture dish or the like. According to the method of the present invention, intestinal epithelial cell-like cells can be obtained from iPS cells by two-dimensional culture. However, three-dimensional culture using a gel-like culture substrate, a three-dimensional culture plate, or the like may be carried out.

A second aspect of the present invention relates to use of the intestinal epithelial cell-like cells prepared by the differentiation inducing method of the present invention. Various assays are provided as the first use. The intestinal epithelial cell-like cells of the present invention can be used for model systems of the intestinal tract, particularly the small intestine, and are useful for evaluating pharmacokinetics (absorption, metabolism, etc.) and toxicity in the intestinal tract, particularly the small intestine. In other words, the intestinal epithelial cell-like cells of the present invention are intended to be used for evaluation of in vivo drug disposition of compounds and evaluation of their toxicity.

Specifically, the absorbability or membrane permeability, drug interaction, induction of a drug metabolizing enzyme, induction of a drug transporter, toxicity, etc. of a test substance can be tested using the intestinal epithelial cell-like cells of the present invention. That is, the present invention provides a method for evaluating the absorbability or membrane permeability, drug interaction, induction of a drug metabolizing enzyme, induction of a drug transporter, toxicity, etc. of a test substance (first embodiment) as a use of the intestinal epithelial cell-like cells. In the method, there are carried out step (i) of preparing a cell layers composed of the intestinal epithelial cell-like cell obtained by the differentiation inducing method of the present invention; step (ii) of bringing a test substance into contact with the cell layers; and step (iii) of quantifying the test substance having permeated the cell layers and evaluating the absorbability or membrane permeability, drug interaction, induction of a drug metabolizing enzyme, induction of a drug transporter, or toxicity of the test substance. The absorbability of the test substance can also be evaluated by a method described below (second embodiment).

In step (i), typically, the intestinal epithelial cell-like cells are cultured on a semi-permeable membrane (porous membrane) to form a cell layers. Specifically, for example, a culture vessel equipped with a culture insert (for example, Transwell (registered trademark) provided by Corning Incorporated) is used to seed and culture cells in the culture insert, whereby a cell layers composed of intestinal epithelial cell-like cells is obtained.

The "contact" in step (ii) is typically carried out by adding the test substance to the medium. The timing of adding the test substance is not particularly limited. Therefore, either the procedure of starting culture in a medium not containing the test substance and then adding the test substance at a certain time point or the procedure of starting culture in a medium containing the test substance in advance may be used.

As the test substance, organic or inorganic compounds having various molecular sizes can be used. Examples of the organic compounds include nucleic acids, peptides, proteins, lipids (simple lipids, complex lipids (phosphoglycerides, sphingolipids, glycosyl glycerides, cerebrosides, etc.)), prostaglandins, isoprenoids, terpenes, steroids, polyphenols, catechins, and vitamins (B1, B2, B3, B5, B6, B7, B9, B12, C, A, D, E, etc.). Existing components or candidate components such as drugs, nutritional foods, food additives, agricultural chemicals, cosmetic products (cosmetics), and the like are also preferable test substances. A plant extract, a cell extract, a culture supernatant, and the like may be used as the test substance. By simultaneously adding two or more kinds of test substances, interactions, synergistic actions, and the like between the test substances may be examined. The test substance may be derived from natural products or obtained by synthesis. In the latter case, for example, an efficient assay system can be constructed by using a combinatorial synthesis technique.

The period during which the test substance is brought into contact can be arbitrarily set. The contact period is, for example, 10 minutes to 3 days, preferably 1 hour to 1 day. Contact may be divided into a plurality of times.

In step (iii), the test substance that has permeated the cell layers is quantified. For example, when a culture vessel equipped with a culture insert, such as Transwell (registered trademark), is used, the test substance that has permeated the culture insert, that is, the test substance that has moved into the upper or lower vessel through the cell layers is quantified by a measuring method such as mass spectrometry, liquid chromatography, an immunological method (e.g., fluorescence immunoassay (FIA), or enzyme immunoassay (EIA)), or the like depending on the test substance. Based on the quantitative result (the amount of the test substance that has permeated the cell layers) and the amount of the test substance used (typically, the amount thereof added to the medium), the absorbability or membrane permeability, drug interaction, induction of a drug metabolizing enzyme, induction of a drug transporter, or toxicity of the test substance is determined and evaluated.

The present invention also provides a method for evaluating the metabolism or absorption of the test substance as another embodiment (second embodiment). In the method, there are carried out step (I) of bringing the test substance into contact with the intestinal epithelial cell-like cell obtained by the differentiation inducing method of the present invention; and step (II) of measuring and evaluating the metabolism or absorption, drug interaction, induction of a drug metabolizing enzyme, induction of a drug transporter, or toxicity of the test substance.

Step (I), that is, the contact of the test substance with the intestinal epithelial cell-like cells can be carried out in the same manner as in the above step (ii). However, it is not indispensable to form a cell layers in advance.

After step (I), the metabolism or absorption, drug interaction, induction of a drug metabolizing enzyme, induction of a drug transporter, or toxicity of the test substance is measured and evaluated (step (II)). Immediately after step (I), that is, after the contact of the test substance, the metabolism or the like may be measured and evaluated either without any substantial time interval or after the lapse of a fixed time (for example, 10 minutes to 5 hours). Metabolism can be measured, for example, by detection of metabolites. In this case, the expected metabolite is usually measured qualitatively or quantitatively using the culture solution after step (I) as a sample. An appropriate method is preferably selected according to the metabolite, and mass spectrometry, liquid chromatography, immunological techniques (for example, fluorescence immunoassay (FIA), enzyme immunoassay (EIA)) and the like can be used as the measurement method.

Typically, when a metabolite of the test substance is detected, it is determined or evaluated that "the test substance has been metabolized". Also, the metabolic expenditure of the test substance can be evaluated according to the amount of the metabolite. The metabolic efficiency of the test substance may be calculated based on the detection result of the metabolite and the amount of the test substance used (typically, the amount thereof added to the medium).

The metabolism of the test substance can be measured using as an index the expression of a drug metabolizing enzyme (cytochrome P450 (particularly, CYP3A4), uridine diphosphate-glucuronosyl transferase (particularly, UGT1A8, UGT1A10), sulfotransferase (particularly, SULT1A3, etc.)) in the intestinal epithelial cell-like cells. Expression of a drug metabolizing enzyme can be evaluated based on the mRNA level or protein level. For example, when an increase in mRNA level of the drug metabolizing enzyme is observed, it can be determined that "the test substance has been metabolized". Similarly, when an increase in activity of the drug-metabolizing enzyme is observed, it can be determined that "the test substance has been metabolized". Quantitative determination and evaluation may be performed based on the expression level of the drug metabolizing enzyme, as in the determination using the metabolite as an index.

In order to evaluate the absorption of the test substance, for example, the amount of the test substance remaining in the culture solution is measured. Normally, the test substance is quantified using the culture solution after step (I) as a sample. An appropriate measurement method may be selected according to the test substance. For example, mass spectrometry, liquid chromatography, an immunological method (e.g., fluorescence immunoassay (FIA), enzyme immunoassay (EIA)), and the like can be adopted. Typically, when a decrease in content of the test substance in the culture solution is observed, it is determined and evaluated that "the test substance has been absorbed". In addition, it is possible to determine and evaluate the absorbed amount of the test substance or the absorption efficiency thereof according to the degree of decrease. Absorption can also be evaluated by measuring the amount of the test substance incorporated into the cells.

The measurement and evaluation of metabolism and the measurement and evaluation of absorption may be carried out simultaneously or in parallel.

As shown in Examples described later, it has been revealed that mucin 2 which is expressed in human small intestinal epithelial cells is highly expressed in the induced pluripotent stem cell-derived intestinal epithelial cell-like cells prepared by the differentiation inducing method of the present invention, at a level not comparable to the level in Caco-2 cells (cells derived from human colon cancer), which are frequently used as a model system of the small intestine. This fact demonstrates that the cells are extremely useful as a model system of the small intestine and shows that the expression of mucin 2 is useful as an index of the assay using the cells. So, the present invention provides, as further embodiments (third embodiment) of the assay using intestinal epithelial cell-like cells, two evaluation methods using expression of mucin 2 as an index, i.e., a method of evaluating the digestive tract mucosa damaging action of the test substance (third embodiment; hereinafter sometimes abbreviated as "damaging action evaluation method") and a method of evaluating the digestive tract mucosa protecting action of the test substance (fourth embodiment; hereinafter sometimes abbreviated as "protecting action evaluation method"). The damaging action evaluation method of the present invention is particularly useful for the prediction of drugs which may cause mucosal damages (ulcers) as side effects (prediction of side effect risk), and the protecting action evaluation method of the present invention is particularly useful for screening for a novel drug having the action of suppressing stress ulcer.

In the damaging action evaluation method (third embodiment) of the present invention, there are carried out step (a) of bringing a test substance into contact with the intestinal epithelial cell-like cell obtained by the differentiation inducing method of the present invention; and step (b) of detecting the expression of mucin 2 in the intestinal epithelial cell-like cell and determining the digestive tract mucosa damaging action of the test substance based on the detection result, wherein a decrease in expression of mucin 2 is indicative for a digestive tract mucosa damaging action of the test substance.

Step (a), that is, the contact of the test substance with the intestinal epithelial cell-like cell can be carried out in the same manner as in the above embodiments (first and second embodiments). However, it is not indispensable to form a cell layers in advance. Usable test substances are also the same as those in the above-described embodiments (first and second embodiments), and the explanation thereof will therefore be omitted.

In step (b) following step (a), the expression of mucin 2 in the intestinal epithelial cell-like cell is detected, and the digestive tract mucosa damaging action of the test substance is determined based on the detection result. In other words, in the present invention, the digestive tract mucosa damaging action of the test substance is determined by utilizing the expression of mucin 2. More specifically, a decrease in expression of mucin 2 is indicative for a digestive tract mucosa damaging action of the test substance. Therefore, when decreased expression of mucin 2 is observed, it is determined that the test substance has the digestive tract mucosa damaging action, whereas, when no decrease in expression of mucin 2 is observed, it is determined that the test substance does not have any digestive tract mucosa damaging action.

The intensity (degree) of the digestive tract mucosa damaging action may be determined based on the degree (level) of the decrease in mucin 2 expression. In addition, when plural of test substances are used, the intensities of the digestive tract mucosa damaging actions of the test substances may be compared and evaluated based on the degree (level) of decrease in mucin 2 expression.

Mucin 2 is a secretory protein. Mucin 2 is a mucous substance involved in the protection of intestinal mucosa, and it is known that reductions in quality and amount of mucin 2 induce ulcerative colitis and cancer.

Expression of mucin 2 may be detected, for example, according to a conventional method. RT-PCR method, real-time PCR method (measurement/quantification of mRNA), immunological methods such as fluorescence immunoassay (FIA) and enzyme immunoassay (EIA), mass spectrometry, and the like can be exemplified as the method of detecting mucin 2.

Typically, intestinal epithelial cell-like cells which are not brought into contact with the test substance (other conditions are identical) (hereinafter referred to as "control") are prepared as comparative controls, and the expression of mucin 2 therein is also detected. Then, by comparing with the expression level of the control, it is determined whether the test substance has decreased the expression of mucin 2. Thus, a more reliable determination result can be obtained by determining the digestive tract mucosa damaging action of the test substance through comparison with the control.

In the protecting action evaluation method (fourth embodiment) of the present invention, there are carried out step (A) of bringing a test substance into contact with the intestinal epithelial cell-like cell obtained by the differentiation inducing method of the present invention; and step (B) of detecting the expression of mucin 2 in the intestinal epithelial cell-like cell and determining the digestive tract mucosa protecting action of the test substance based on the detection result, wherein a increase in expression of mucin 2 by the substance is indicative for a digestive tract mucosa protecting action of the test substance.

In step (A), contact of the test substance with the intestinal epithelial cell-like cell is performed. The contact of the test substance with the intestinal epithelial cell-like cell can be carried out in the same manner as in the above embodiment (third embodiment).

Usable test substances are the same as those in the above-described embodiments (first and second embodiments), and the explanation thereof will therefore be omitted.

In step (B) following step (A), the expression of mucin 2 in the intestinal epithelial cell-like cell is detected, and the digestive tract mucosa protecting action of the test substance is determined based on the detection result. That is, in the present invention, the digestive tract mucosa protecting action of the test substance is determined by utilizing the expression of mucin 2. More specifically, a increase in expression of mucin 2 by the substance is indicative for a digestive tract mucosa protecting action of the test substance. Therefore, when increased expression of mucin 2 is observed, it is determined that the test substance has the digestive tract mucosa protecting action, whereas, when no increase in expression of mucin 2 is observed, it is determined that the test substance does not have any digestive tract mucosa protecting action. The intensity (degree) of the digestive tract mucosa protecting action may be determined based on the degree (level) of the increase in mucin 2 expression. In addition, when a plurality of test substances are used, the intensities of the digestive tract mucosa protecting actions of the test substances may be compared and evaluated based on the degree (level) of increase in mucin 2 expression.

As with the above embodiment (third embodiment), it is preferable to provide a comparative control (control) and to determine the digestive tract mucosa protecting action of the test substance by comparison with the control, in order to obtain a more reliable determination result. As the control in this case, intestinal epithelial cell-like cells which are not brought into contact with the test substance (other conditions are identical) can be used.

The evaluation method of this embodiment (fourth embodiment) is useful for screening for a novel drug for preventing or treating mucosal damage or stress ulcer as a side effect of the drug, for example. When the evaluation method of the present invention is used for screening, an effective test substance is selected on the basis of the determination result in step (B). When the selected substance has sufficient medicinal effect, the substance can be used as it is as an active ingredient of intestinal mucosa protecting agent. On the other hand, when the selected substance does not have sufficient medicinal effect, it can be used as an active ingredient of an intestinal mucosa protecting agent after applying modification such as chemical modification to enhance its efficacy. Of course, even when it has sufficient medicinal effect, similar modification may be applied for the purpose of further increasing the medicinal effect.

A cell preparation containing the intestinal epithelial cell-like cells is provided as a second use of the intestinal epithelial cell-like cells prepared by the differentiation inducing method of the present invention. The cell preparation of the present invention is applicable to the treatment of various intestinal diseases. In particular, use as a material for regeneration/reconstruction of damaged (including dysfunction) intestinal epithelial tissue is contemplated. That is, contribution to regenerative medicine can be expected. The cell preparation of the present invention can be prepared, for example, by suspending the intestinal epithelial cell-like cells obtained by the method of the present invention in physiological saline, buffer solution (for example, phosphate buffer), or the like, or by preparing a three-dimensional tissue (organoids or spheroids) using the cells. For example, $1 \times 10^5$ to $1 \times 10^{10}$ cells may be contained as an amount of a single dose so that a therapeutically effective amount of the cells can be administered. The content of the cells can be appropriately adjusted in consideration of the purpose of use, target disease, sex, age, and body weight of the recipient, state of the affected part, state of the cells, and the like.

Dimethyl sulfoxide (DMSO), serum albumin, and the like may be contained in the cell preparation of the present invention for the purpose of protecting the cells; antibiotics and the like may be contained therein for the purpose of inhibiting bacterial contamination; various components (vitamins, cytokines, growth factors, steroids, etc.) may be contained therein for the purpose of cell activation, proliferation or induction of differentiation. In addition, other pharmaceutically acceptable components (e.g., carriers, excipients, disintegrators, buffers, emulsifiers, suspending agents, soothing agents, stabilizers, preservatives, antiseptic agents, and physiological saline) may be contained in the cell preparation of the present invention.

EXAMPLES

A. Search for Small Molecule Compounds Useful for Promoting Differentiation of Human iPS Cells into Intestinal Epithelial Cells/Acquiring Functions For the purpose of preparing cells (intestinal epithelial cell-like cells) exhibiting functions close to those of the intestinal epithelial cells of living bodies easily and at low cost, the usefulness of new small molecule compounds having an action which is different from that of the small molecule compounds reported earlier, on differentiation from human iPS cells into intestinal epithelial cells, was studied. The pharmacokinetic functions of intestinal epithelial cell-like cells prepared using the compounds identified to be useful was also studied.

1. Method (1) Cell

Human iPS cells (iPS-51: Windy) were prepared by introducing octamer binding protein 3/4 (OCT 3/4), sex determining region Y-box 2 (SOX2), kruppel-like factor 4 (KLF4), and v-myc myelocytomatosis viral oncogene homolog (avian) (c-MYC) into human embryonic lung fibroblasts MRC-5 using pantropic retroviral vectors and cloning human ES cell-like colonies, and were provided by Dr. Akihiro Umezawa of the National Center for Child Health and Development. Mouse embryonic fibroblasts (MEFs) were used as feeder cells.

(2) Medium

For MEF culture, a Dulbecco Modified Eagle's Medium (DMEM) containing 10% fetal bovine serum (FBS), 2 mmol/L L-glutamine (L-Glu), 1% non-essential amino acid (NEAA), 100 units/mL penicillin G, and 100 µg/mL streptomycin was used. As a dissociation solution for MEF, 0.05% trypsin-ethylenediaminetetraacetic acid (EDTA) was used, and Cell Banker 1 was used as a preservation solution for MEF. For maintenance culture of human iPS cells, DMEM Ham's F-12 (DMEM/F 12) containing 20% knockout serum replacement (KSR), 0.8% NEAA, 2 mmol/L L-Glu, 0.1 mmol/L 2-mercaptoethanol (2-MeE), and 5 ng/mL fibroblast growth factor (FGF) 2 was used. Dulbecco's phosphate buffered saline (PBS) containing 1 mg/mL collagenase IV, 0.25% trypsin, 20% KSR, and 1 mmol/L calcium chloride was used as a dissociation solution for human iPS cells. A cryopreservation solution for primate ES/iPS cells was used as a preservation solution for human iPS cells.

(3) Culture of Human iPS Cells

Human iPS cells were seeded on Mitomycin C-treated MEF ($6\times10^5$ cells/100 mm dish) and cultured at 37° C. in a $CO_2$ incubator under the 5% $CO_2$/95% air condition. Passage of human iPS cells was performed at a split ratio of 1:2 to 1:3 after culture for 3 to 5 days. For human iPS cells, the medium was exchanged after 48 hours from thawing and, thereafter, exchanged daily.

(4) Differentiation of Human iPS Cells into Intestinal Epithelial Cells

Differentiation of human iPS cells into intestinal epithelial cells was initiated in a state where the proportion of undifferentiated colonies of the human iPS cells in the culture dish arrived at about 70%. The cells were cultured in Roswell Park Memorial Institute (RPMI)+GlutaMAX medium containing 0.5% FBS, 100 ng/mL activin A, 100 units/mL penicillin G, and 100 µg/mL streptomycin for 2 days and in RPMI+GlutaMAX medium containing 2% FBS, 100 ng/mL activin A, 100 units/mL penicillin G, and 100 µg/mL streptomycin for 1 day to be differentiated into endoderm. Thereafter, the endoderm was cultured in DMEM/F12 containing 2% FBS, 1% GlutaMAX, and 250 ng/mL FGF2 for 4 days to be differentiated into intestinal stem cells. After this treatment, Y-27632 (Rho-binding kinase inhibitor) was added to a concentration of 10 µmol/L, and the cells treated for 60 minutes at 37° C. in a $CO_2$ incubator under the 5% $CO_2$/95% air condition were dissociated with Accutase and seeded on a 24-well plate for cell culture which was coated with Matrigel matrix Growth Factor Reduced diluted 30-fold with a human iPS cell medium in advance. Thereafter, the cells were cultured in DMEM/F12 containing 2% FBS, 2 mmol/L L-Glu, 1% NEAA, 2% B27 supplement, 1% N2 supplement, 100 units/mL penicillin G, 100 µg/mL streptomycin, 20 ng/mL epidermal growth factor (EGF), and 10 µmol/L Y-27632 for 1 day, and cultured in DMEM/F12 containing 2% FBS, 2 mmol/L L-Glu, 1% NEAA, 2% B27 supplement, 1% N2 supplement, 100 units/mL penicillin G, 100 µg/mL streptomycin, and 20 ng/mL epidermal growth factor (EGF) for 18 days to be differentiated into intestinal epithelial cells. The treatment with the inducer of the drug-metabolizing enzyme was performed by adding, into DMEM/F12 containing 2% FBS, 2 mmol/L L-Glu, 1% NEAA, 2% B27 supplement, 1% N2 supplement, 100 units/mL penicillin G, 100 µg/mL streptomycin, and 20 ng/mL EGF, 1α,25-dihydroxyvitamin D3 (VD3) so as to arrive at a concentration of 10 nmol/L or 100 nmol/L or rifampicin so as to arrive at a concentration of 10, 40, or 100 µmol/L, and culturing the cells for 48 hours before termination of the differentiation. Also, in addition to the small molecule compounds PD98059 (20 µmol/L), 5-aza-2'-deoxycytidine (5 µmol/L) and A-83-01 (0.5 µmol/L) previously found by us, 1 mmol/L 8-bromo-3',5'-cyclic adenosine monophosphate (8-Br-cAMP) or 0.5 mmol/L 3-isobutyl-1-methylxanthine (IBMX) were added at the time of differentiation to study their effect on differentiation into intestinal stem cells and intestinal epithelial cells.

(5) Total Ribonucleic Acid (RNA) Extraction

The total RNA was extracted according to the attached manual of RNeasy (registered trademark) Mini Kit (Qiagen), after completion of induction of differentiation of human iPS cells.

(6) Reverse Transcription Reaction

PrimeScript (registered trademark) RT reagent Kit (Perfect Real Time) (Takara Bio Inc.) was used for synthesis of complementary DNA (cDNA). The operation was in accordance with the attached manual.

(7) Real-Time Reverse Transcription Polymerase Chain Reaction (Real-Time RT-PCR)

Real-Time RT-PCR was performed with SYBR (registered trademark) Premix Ex Taq II (Perfect Real Time) (Takara Bio Inc.) using cDNA as a template. The operation was in accordance with the attached manual. Glyceraldehyde-3-phosphate dehydrogenase (GAPDH) was used as an endogenous control to correct the measurement results.

(8) Experiment on Uptake of Glycylsarcosine (Gly-Sar) and Estrone-3-Sulfate (ES)

After completion of induction of differentiation, incubation was performed at 37° C. or 4° C. with an uptake solution containing tritium-labeled Gly-Sar or ES. In the Gly-Sar uptake experiment, there was used an uptake solution containing 137 mmol/L sodium chloride, 5.4 mmol/L potassium chloride, 0.81 mmol/L magnesium sulfate, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose and 10 mmol/L MES and having a pH of 6.0. In the ES uptake experiment, there was used an uptake solution containing 137 mmol/L sodium chloride, 5.4 mmol/L potassium chloride, 0.81 mmol/L magnesium sulfate, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose, and 10 mmol/L HEPES and having a pH of 7.4. After completion of incubation, uptake was stopped by washing the cells with the ice-cold uptake solution. Thereafter, the cells were solubilized with a 0.2 M sodium hydroxide solution containing 0.5% sodium dodecyl sulfate (SDS), and a scintillation solution was added. The intracellular uptake of Gly-Sar or ES was calculated from the radioactivity measured using a liquid scintillation counter.

(9) Experiment on Transport of Hoechst 33342 and Digoxin

After completion of induction of differentiation, an uptake solution containing Hoechst 33342 or tritium-labeled digoxin was added to the apical membrane side or basolateral membrane side of the cell culture inserts, incubated at 37° C., and sampled, over time, from a chamber opposite to the side to which the solution was added. In the transport experiment, an uptake solution containing 137 mmol/L sodium chloride, 5.4 mmol/L potassium chloride, 0.81 mmol/L magnesium sulfate, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose, and 10 mmol/L HEPES and having pH 7.4 was used. The apparent membrane permeability coefficient of Hoechst 33342 was calculated from the fluorescence intensity measured using a fluorescent plate reader (excitation wavelength: 355 nm; fluorescence wavelength: 460 nm), and the apparent membrane permeability coefficient of digoxin was calculated from the radioactivity measured using a liquid scintillation counter. The efflux ratio was calculated by dividing the apparent membrane permeability coefficient from the basolateral membrane side to the apical membrane side by the apparent membrane permeability coefficient from the apical membrane side to the basolateral membrane side. The transepithelial electrical resistance (TEER) value was measured using Millicell ERS-2.

(10) Experiment on Drug Metabolism

After completion of induction of differentiation, a medium containing 100 µmol/L midazolam (DMEM/F12 containing 2 mmol/L L-Glu, 1% NEAA, 1% N2 supplement, 100 units/mL penicillin G, 100 µg/mL streptomycin, and 20 ng/mL EGF) was subjected to incubation at 37° C., and, after lapse of a predetermined time, sampled. The metabolic activity was calculated from the amount of 1-hydroxymidazolam in the medium measured using a liquid chromatography-mass spectrometer (LC-MS/MS). After completion of the experiment on metabolism, protein quantification was carried out, and the metabolic activity was corrected by the amount of protein.

The characteristics of the marker genes used in this study are shown below.

ABCB1/MDR1 (ATP binding cassette transporter B1/multidrug resistant protein 1): It is a P-glycoprotein and functions as an efflux transporter.

ABCG2/BCRP (ATP binding cassette transporter G2/breast cancer resistant protein): It functions as an efflux transporter.

CYP3A4 (Cytochrome P450 3A4): It is a major drug metabolizing enzyme in the small intestine.

LGR5 (leucine-rich repeat containing G-protein-coupled receptor 5): It is a marker for intestinal stem cells.

PXR (pregnane X receptor): It is involved in expression and induction of CYP3A4.

SLC15A1/PEPT1 (SLC (solute carrier) family member 15A1/peptide transporter 1): It is expressed on the apical membrane side of the small intestine.

SLCO2B1/OATP2B1 (SLC (solute carrier) organic anion transporter 2B1): It is expressed on the apical membrane side of the small intestine.

Sucrase-isomaltase: It is a disaccharidase present in intestinal epithelia and is an intestinal epithelium-specific marker.

UGT1A1 (uridine diphosphate-glucuronosyl transferase 1A1): It is involved in glucuronic acid conjugation of the drugs.

UGT1A4 (uridine diphosphate-glucuronosyl transferase 1A4): It is involved in the glucuronic acid conjugation of the drug.

Villin 1: It is a major constituent of microvilli.

Figure 2:
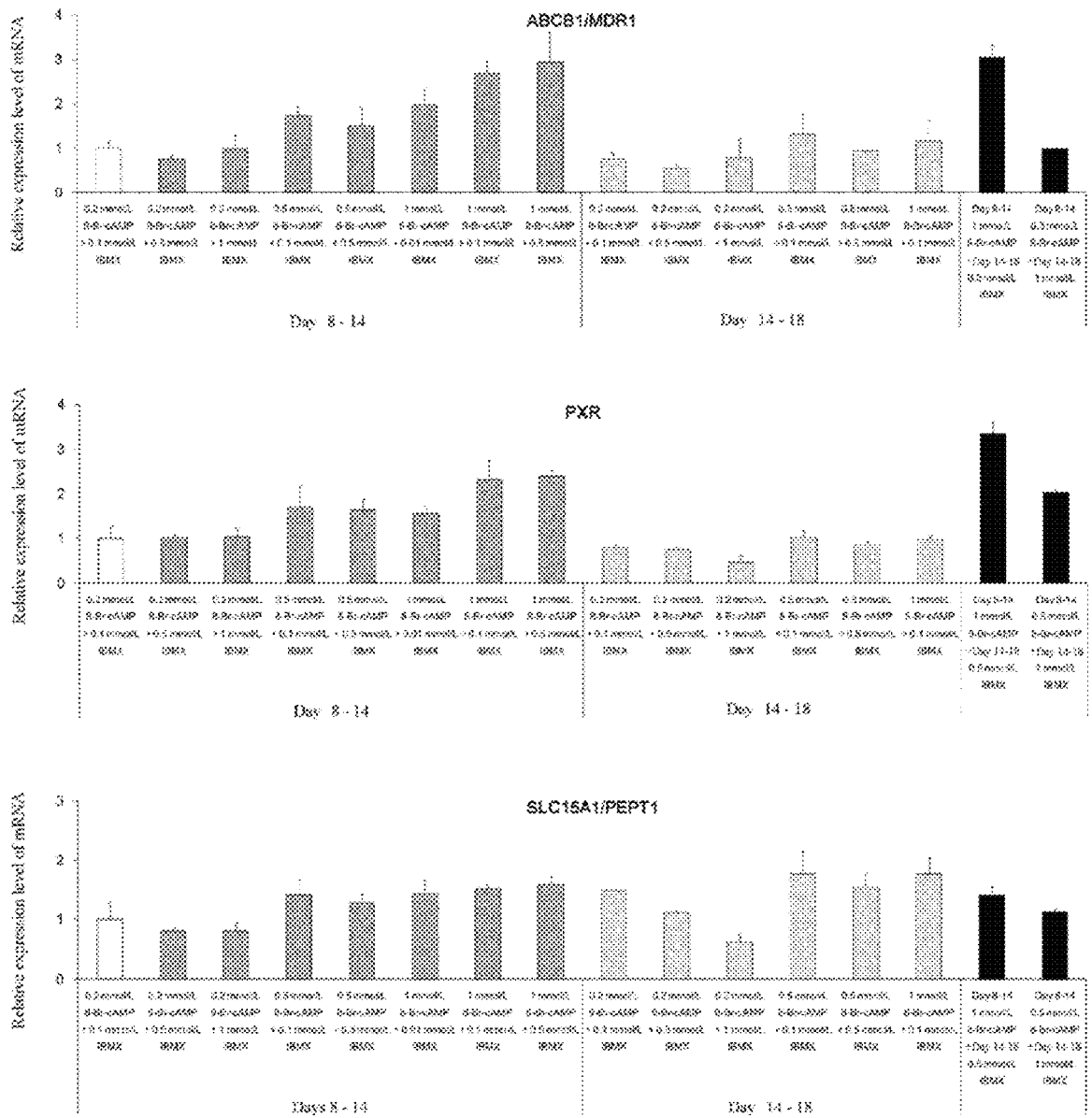
FIG. 2 is a continuation of FIG. 1.

2. Results (1) Study on Condition for Differentiation into Intestinal Epithelial Cells Studied were the concentrations of 8-Br-cAMP and IBMX to be added at the time of induction of differentiation from human iPS cells into intestinal epithelial cells and the period of the addition thereof. As a result, 8-Br-cAMP was used at 1 mmol/L between the 8th day and the 14th day after the start of differentiation, and IBMX was used at 0.5 mmol/L between the 14th day and the 18th day after the start of differentiation, so that the mRNA expression levels of the efflux transporter ABCB1/MDR1, peptide uptake transporter SCL15A1/PEPT1, a major drug metabolizing enzyme cytochrome P450 (CYP) 3A4, and pregnane X receptor (PXR), which is a nuclear receptor involved in the expression of CYP3A4, were high (FIGS. 1 and 2). Therefore, 8-Br-cAMP was decided to be added in a concentration of 1 mmol/L between the 8th day and the 14th day after the start of differentiation, and IBMX was decided to be added in a concentration of 0.5 mmol/L between the 14th day and the 23th day after the start of differentiation.

Figure 3:
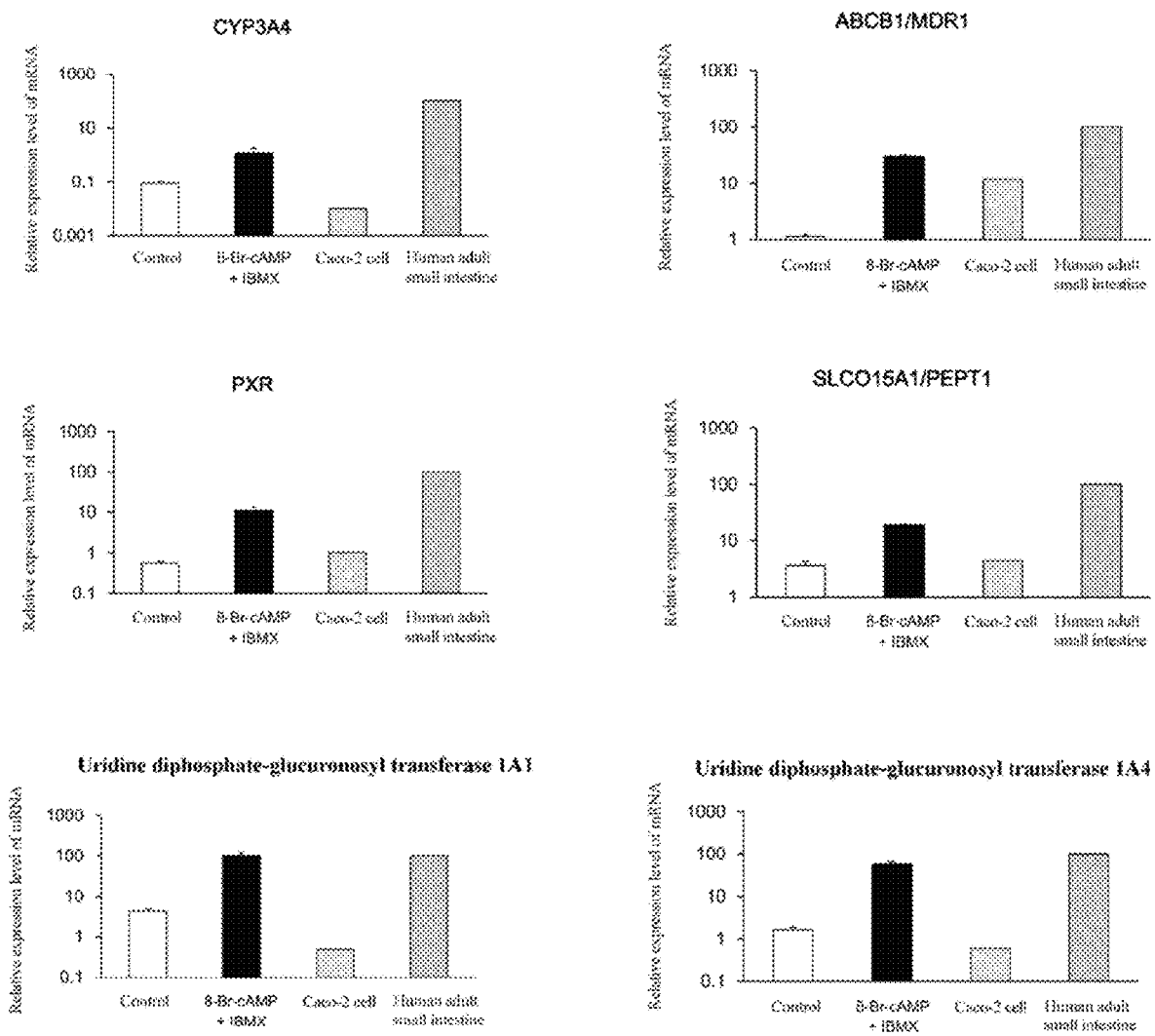
FIG. 3 shows effects of 8-Br-cAMP and IBMX on expression of various marker genes in the differentiated intestinal epithelial cell-like cells. Expressed by average value±S.D. (n=3). Control is a group without addition of 8-Br-cAMP or IBMX.
Figure 4:
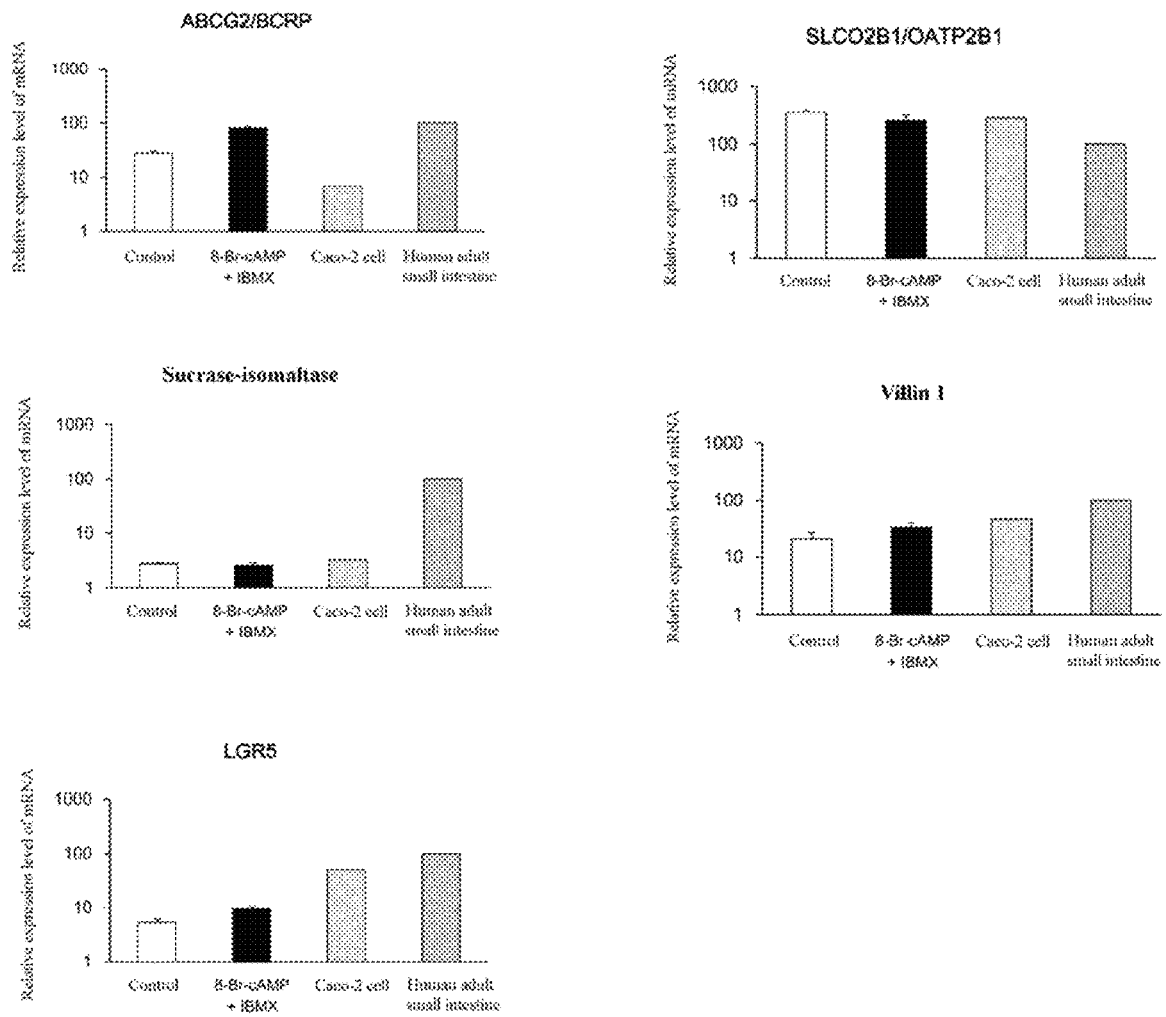
FIG. 4 is a continuation of FIG. 3.

Next, the expression of the intestinal stem cell markers, intestinal tract markers, and pharmacokinetics-related genes when 8-Br-cAMP and IBMX were added under the above conditions was analyzed. As a result, compared to the control, the expression of mRNA increased 17 times for CYP3A4, 30 times for ABCB1/MDR1, 20 times for PXR, 5 times for SLC15A1/PEPT1, 20 times for uridine diphosphate-glucuronosyl transferase (UGT) 1A1, 40 times for UGT1A4, and about 3 times for ABCG2/BCRP (FIGS. 3 and 4).

Figure 5:
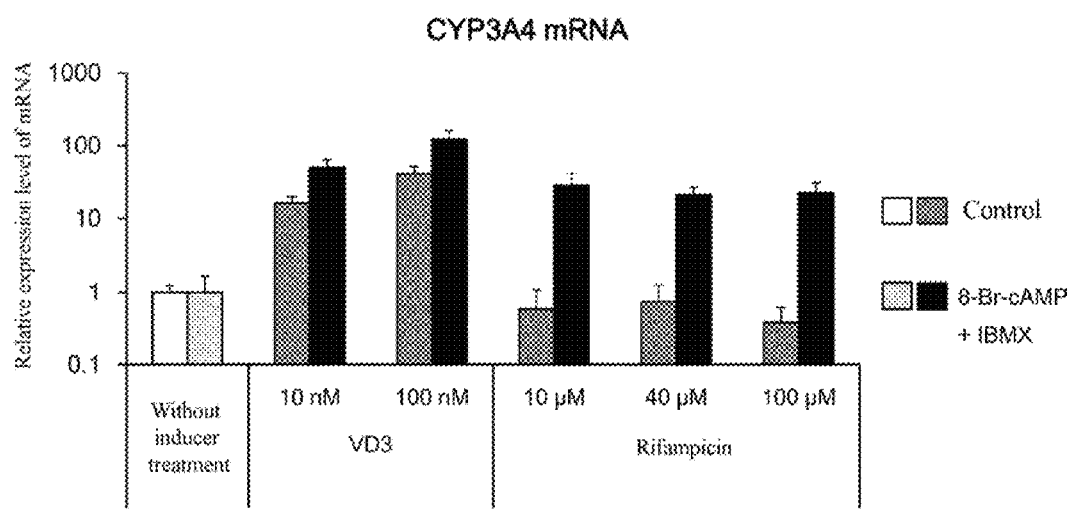
FIG. 5 shows induction of CYP3A4 expression in the differentiated intestinal epithelial cell-like cells. Expressed by average value±S.D. (n=3). Control is a group without addition of 8-Br-cAMP or IBMX.

(2) Evaluation of CYP3A4 Inducibility and Activity in Differentiated Intestinal Epithelial Cell-Like Cells Studied was the induction of CYP3A4 expression using the CYP3A4 inducers, 1α,25-dihydroxyvitamin D3 (VD3) and rifampicin. As a result, the induction of CYP3A4 by 1α,25-dihydroxyvitamin D3 was observed in both the intestinal epithelial cell-like cells induced to differentiate by the conventional differentiation method and the intestinal epithelial cell-like cells induced to differentiate using 8-Br-cAMP and IBMX (FIG. 5). On the other hand, the induction of CYP3A4 expression by rifampicin was not observed in the intestinal epithelial cell-like cells induced to differentiate by the conventional differentiation method, but, by induction of differentiation using 8-Br-cAMP and IBMX, the cells began to have the response by rifampicin.

Figure 6:
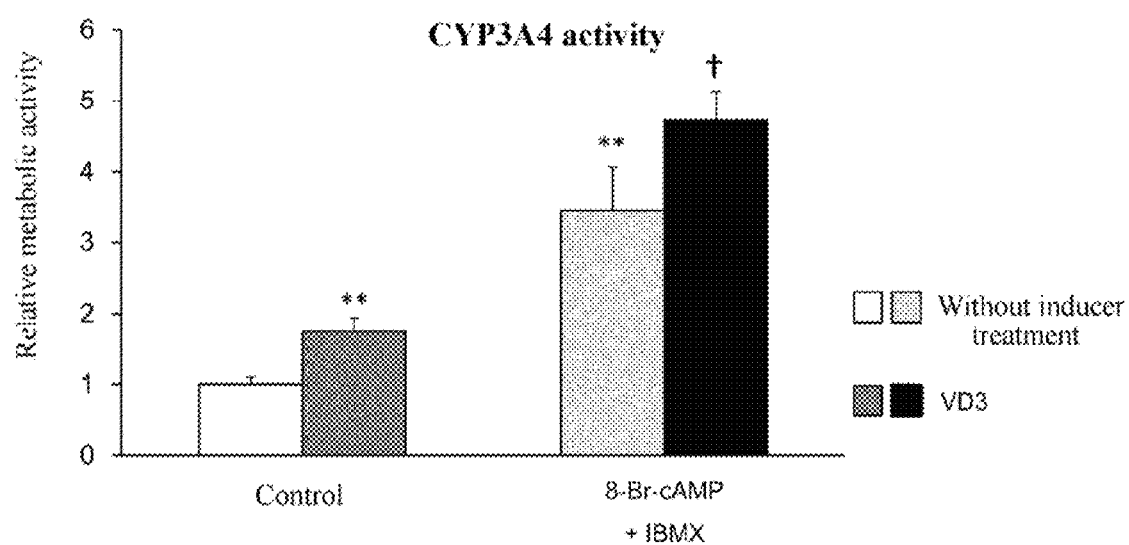
FIG. 6 shows a metabolic activity of midazolam in the differentiated intestinal epithelial cell-like cells (CYP3A4 metabolic activity). Expressed by average value±S.D. (n=3). ** $P<0.01$ vs control group (without inducer treatment), † $P<0.05$ vs. 8-Br-cAMP+IBMX group (without inducer treatment), the control is a group without addition of 8-Br-cAMP or IBMX. Midazolam was added at 100 µmol/L. 1α,25-Dihydroxyvitamin $D_3$ (VD3) was added at 10 nmol/L.

Next, the activity of CYP3A4 was evaluated from the amount of metabolite (1-hydroxide) of midazolam which is a typical substrate of CYP3A4. As a result, the activity of CYP3A4 significantly increased in the group without inducer treatment for the intestinal epithelial cells induced to differentiate using 8-Br-cAMP and IBMX, as compared with the intestinal epithelial cells induced to differentiate by the conventional differentiation method (FIG. 6). In addition, the activity of CYP3A4 significantly increased upon treatment with 1α,25-dihydroxyvitamin D3 (VD3) in the cells induced to differentiate using 8-Br-cAMP and IBMX.

Figure 7:
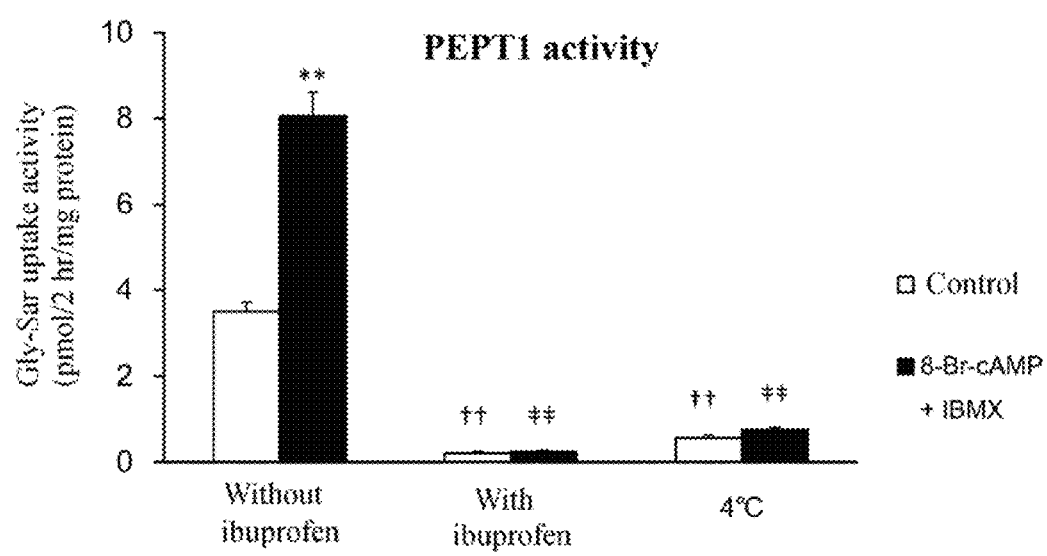
FIG. 7 shows uptake of glycylsarcosine (Gly-Sar) in the differentiated intestinal epithelial cell-like cells (PEPT1 transport activity). Expressed by average value±S.D. (n=3). ** $P<0.01$ and †† $P<0.01$ vs control group (without ibuprofen), ‡‡ $P<0.01$ versus 8-Br-cAMP+IBMX group (without ibuprofen), the control is a group without addition of 8-Br-cAMP+IBMX. Ibuprofen was added at 3 mmol/L.

(3) Evaluation of Function of Uptake Transporters in Differentiated Intestinal Epithelial Cell-Like Cells The activity of the peptide uptake transporter PEPT1 was evaluated using its substrate glycylsarcosine (Gly-Sar). In order to evaluate whether this uptake was mediated by the transporter, uptake experiments were carried out also in the presence of ibuprofen as a PEPT1 inhibitor and under the condition of 4° C. at which the function of the transporter was suppressed. As a result, Gly-Sar uptake significantly reduced in the presence of ibuprofen and under the condition of 4° C., in both the intestinal epithelial cell-like cells induced to differentiate by the conventional differentiation method and the intestinal epithelial cell-like cells induced to differentiate using 8-Br-cAMP and IBMX (FIG. 7). Furthermore, Gly-Sar uptake significantly increased in the ibuprofen-untreated group (control group) of the intestinal epithelial cells induced to differentiate using 8-Br-cAMP and IBMX, as compared with the conventional differentiation method. This demonstrated that the PEPT1 activity increased by inducing differentiation using 8-Br-cAMP and IBMX.

Figure 8:
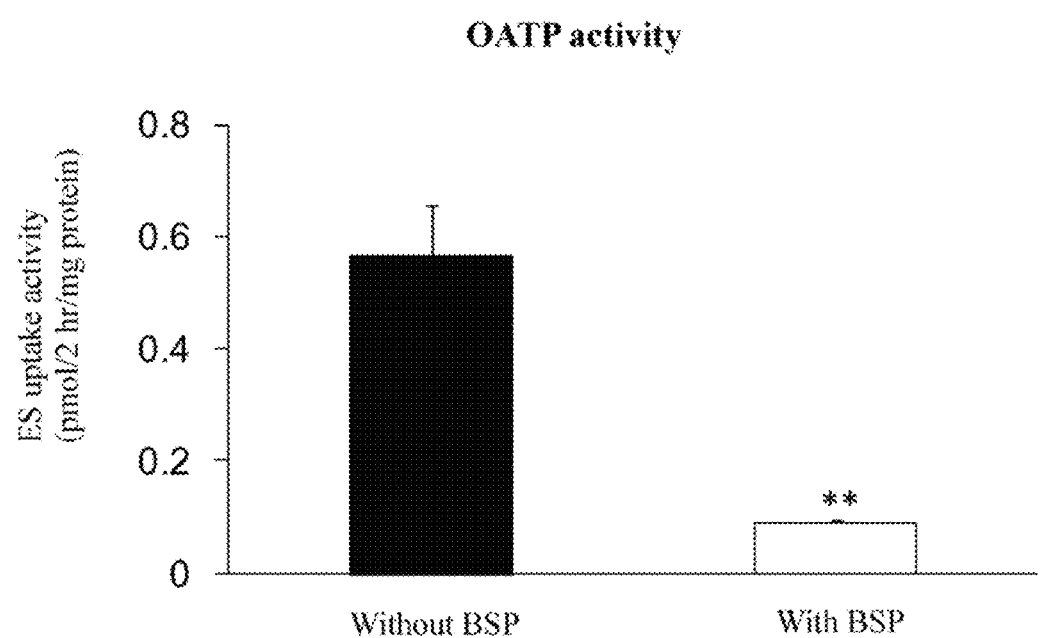
FIG. 8 shows uptake of estrone-3-sulfate (ES) in the differentiated intestinal epithelial cell-like cells (OATP transport activity). Expressed by average value±S.D. (n=3). ** $P<0.01$ vs without BSP. Bromsulphthalein (BSP) was added at 0.2 mmol/L.

The activity of the organic anion transporter OATP was evaluated using its substrate estrone-3-sulfate (ES) in the presence or absence of the inhibitor bromsulphthalein (BSP). As a result, the uptake of ES in the presence of BSP significantly reduced in the intestinal epithelial cell-like cells induced to differentiate using 8-Br-cAMP and IBMX. This demonstrated that the cells had the OATP activity (FIG. 8).

Figure 9:
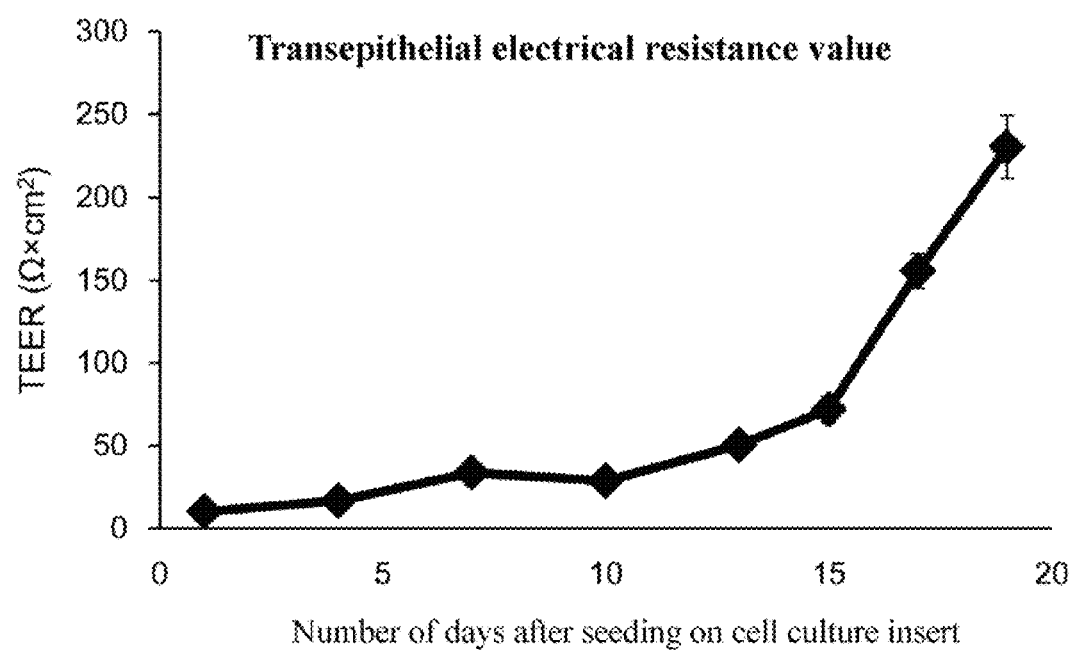
FIG. 9 shows a time course of the transepithelial electrical resistance (TEER) value of the differentiated intestinal epithelial cell-like cells. Expressed by average value±S.D. (n=3).

(4) Evaluation of Function of Efflux Transporters in Differentiated Intestinal Epithelial Cell-Like Cells When the transepithelial electrical resistance (TEER) value of the intestinal epithelial cell-like cells induced to differentiate using 8-Br-cAMP and IBMX on the cell culture inserts was measured, an increase in TEER value over time was observed as the differentiation progressed, and, finally, the value reached 200-250$\Omega \times cm^2$ (FIG. 9).

Figure 10:
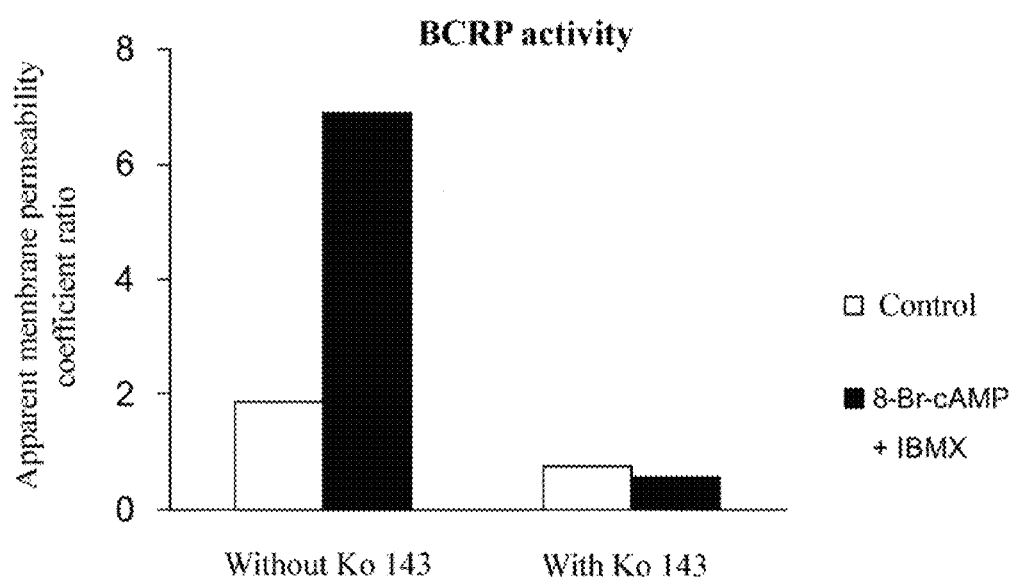
FIG. 10 shows transport of Hoechst 33342 in the differentiated intestinal epithelial cell-like cells (BCRP transport activity). Expressed by average value±S.D. (n=3). Control is a group without addition of 8-Br-cAMP or IBMX. Hoechst 33342 was added at 20 µmol/L. Ko 143 was added at 10 µmol/L.

The function of the efflux transporter BCRP was studied using the intestinal epithelial cell-like cells induced to differentiate on the cell culture insert. Hoechst 33342 was used as a substrate of BCRP, and Ko 143 was used as an inhibitor thereof. Based on the obtained apparent membrane permeability coefficients, their ratio was calculated to evaluate the activity of BCRP. As a result, the treatment with Ko 143 decreased the apparent membrane permeability coefficient ratio in both the intestinal epithelial cell-like cells induced to differentiate by the conventional differentiation method and the intestinal epithelial cell-like cells induced to differentiate using 8-Br-cAMP and IBMX (FIG. 10). As compared with the conventional differentiation method, the apparent membrane permeability coefficient ratio increased in the absence of Ko 143 in the intestinal epithelial cell-like cells induced to differentiate using 8-Br-cAMP and IBMX, which suggested that the cells had a higher BCRP activity.

Figure 11:
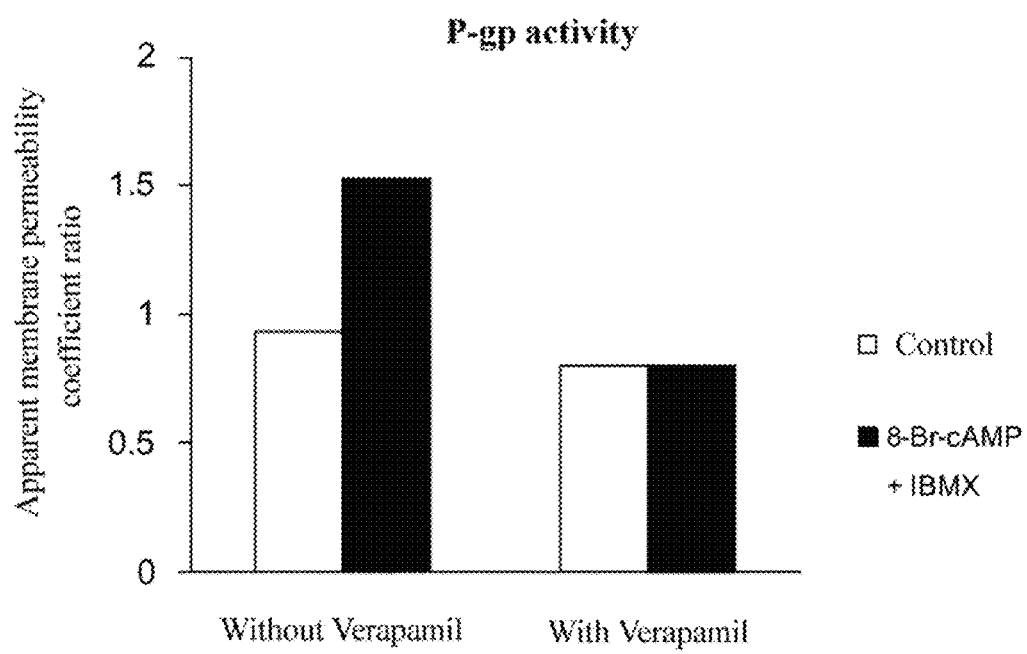
FIG. 11 shows transport of digoxin in the differentiated intestinal epithelial cell-like cells. Expressed by average value±S.D. (n=3). Control is a group without addition of 8-Br-cAMP or IBMX. Verapamil was added at 10 µmol/L.

As earlier, the function of the efflux transporter P-gp was studied using the intestinal epithelial cell-like cells induced to differentiate on the cell culture insert. Digoxin was used as a substrate of P-gp, and verapamil was used as an inhibitor thereof. As a result, as compared with the conventional differentiation method, the apparent membrane permeability coefficient ratio increased in the absence of verapamil in the intestinal epithelial cells induced to differentiate using 8-Br-cAMP and IBMX, and the treatment with verapamil decreased the ratio (FIG. 11). This demonstrated that the P-gp activity, which could not be detected by the conventional differentiation method, could be detected.

From the above results, it has been revealed that the condition that cAMP is supplied to the cells (specifically, for example, 8-Br-cAMP is added to the medium) and the condition for suppressing the decrease in intracellular cAMP concentration (specifically, the cAMP-degrading enzyme inhibitor (e.g., IBMX) is added to the medium) promote the differentiation into intestinal epithelial cells, and, in particular, are effective for acquiring functions as intestinal epithelial cells (maturation). In addition to the previously reported conditions, i.e., the combined use of a MEK1 inhibitor, a DNA methyltransferase inhibitor and a TGF-β receptor inhibitor, by using these conditions singly or in combination, more functional intestinal epithelial cell-like cells can be obtained.

3. Conclusion

As described above, intestinal epithelial cell-like cells having, in addition to the drug metabolizing enzyme activity and induction ability, the transport functions of the uptake and efflux transporters were successfully prepared from human iPS cells by a simple method. The conditions effective for promoting differentiation and acquiring functions were successfully found.

B. Study on Properties of Intestinal Epithelial Cell-Like Cells Derived from Human iPS Cells In order to investigate further usefulness of iPS cell-derived intestinal epithelial cell-like cells, attention was focused on mucin 2, which is a mucous substance involved in the protection of intestinal mucosa, and the expression state of mucin 2 in the iPS cell-derived intestinal epithelial cell-like cells was investigated.

1. Method

<Mucosa Damaging Action>

In the process of differentiation into intestinal epithelial cells, meloxicam (50 μM, 200 μM), indomethacin (75 μM, 300 μM), and ketoprofen (200 μM, 800 μM) known as NSAIDs and having the mucosa damaging action were each added for 6 days and cultured to study the change in expression of mucin 2.

<Mucosa Protecting Action>

In the process of differentiation into intestinal epithelial cells, irsogladine (10 μM, 40 μM) and rebamipide (50 μM, 100 μM, 250 μM, 1000 μM) having the mucosa protecting action were each added for 6 days and cultured to study the change in expression of mucin 2.

<RNA Extraction>

After completion of collection of the differentiated intestinal epithelial cells, RNA was extracted according to the attached manual of Agencourt (registered trademark) RNAdvance Tissue Kit.

<Reverse Transcription Reaction>

Synthesis of complementary DNA (cDNA) was performed according to the attached manual using ReverTra Ace (registered trademark) qPCR RT Master Mix.

<Real-Time Reverse Transcription Polymerase Chain Reaction (Real-Time RT-PCR)>

For Real-Time RT-PCR, KAPA SYBR Fast qPCR Kit was used, cDNA was used as a template, and the reaction was carried out according to the attached manual. Results were corrected using hypoxanthine-guanine phosphoribosyltransferase (HPRT) as an endogenous control.

2. Results and Discussion

Figure 12:
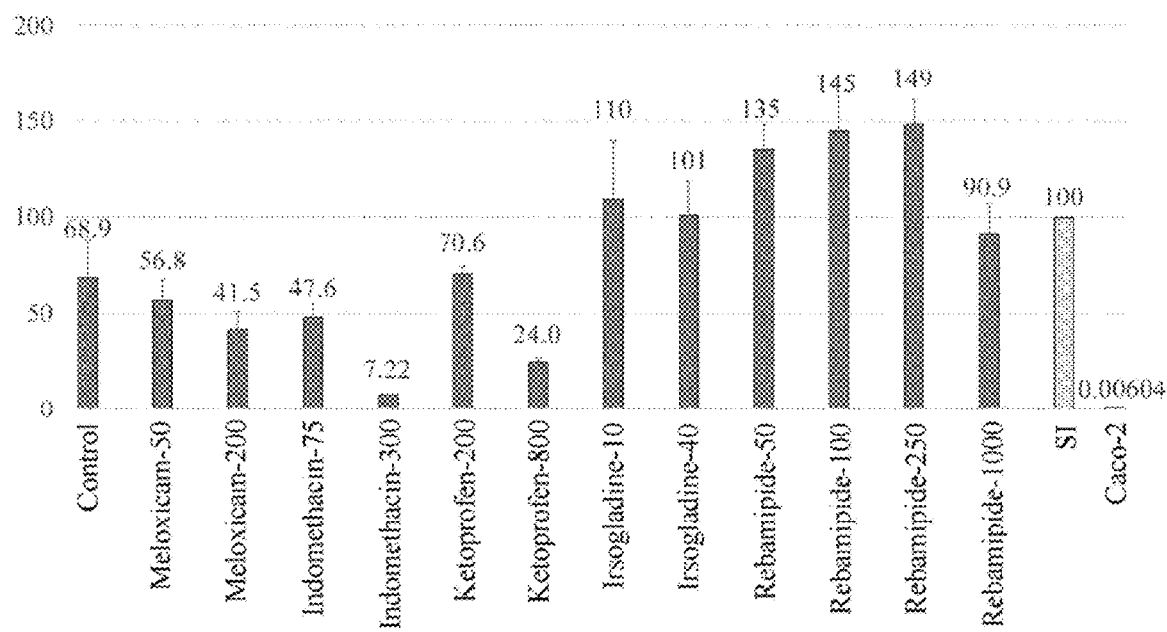
FIG. 12 shows expression (mRNA level) of mucin 2 in the differentiated intestinal epithelial cell-like cells and results of assays using the same. The vertical axis indicates the relative value based on the expression level of commercially available human small intestine cells (SI) (100). Average value±standard deviation (n=3)

The detection results of mucin 2 mRNA is shown in FIG. 12. The intestinal epithelial cell-like cells (Control) prepared by the present method highly expressed mucin 2, which was hardly expressed in Caco-2 cells (Caco-2) derived from human colon cancer. The expression level reaches about 70% of the expression level of commercially available human small intestine-derived cells (SI). This fact indicates that the intestinal epithelial cell-like cells prepared by the present method are quite highly useful as a model system of the small intestine.

By adding NSAIDs, the expression (mRNA level) of mucin 2 in the intestinal epithelial cell-like cells prepared by the present method was decreased (except for ketoprofen-200). Among NSAIDs, the addition of the COX-2 selective inhibitor meloxicam showed a moderate decrease in mucin 2 expression (mRNA level) as compared with other NSAIDs (nonselective COX inhibitors). This is a result reflecting close relationship of mucosal damage with COX-1 inhibition. On the other hand, the expression (mRNA level) of mucin 2 increased when irsogladine and rebamipide, which are known to have the mucosa protecting action, were added. The above results indicate that the intestinal epithelial cell-like cells prepared by the present method are useful for assays using as an index the expression of mucin 2 (system of prediction of a drug causing mucosal damages (ulcers) (prediction of side effect risk) and screening for a drug having the mucosa protecting action).

INDUSTRIAL APPLICABILITY

According to the present invention, more functional intestinal epithelial cell-like cells can be easily and efficiently prepared from iPS cells. Intestinal epithelial cell-like cells are useful as a model system of the small intestine and can be used for evaluation of absorption/metabolism/membrane permeability, induction of drug metabolizing enzymes, induction of drug transporters, toxicity, and the like. The cells are also expected to be used as an active ingredient of cell preparation for the treatment of various intestinal diseases or as a material for regenerative medicine.

The present invention is not limited to the description of the embodiments and examples of the present invention at all. Various modifications that can be easily achieved by those skilled in the art without departing from the claims also fall within the scope of the invention. The contents of the articles, patent laid-open publications, patent publications, and the like specified herein shall be cited by incorporation in their entirety.

The invention claimed is:

1. A method of inducing differentiation of induced pluripotent stem cells into intestinal epithelial cells, comprising:
    step (1) of differentiating induced pluripotent stem cells into endoderm-like cells;
    step (2) of differentiating the endoderm-like cells obtained in step (1) into intestinal stem cell-like cells: and
    step (3) of differentiating intestinal stem cell-like cells obtained in step (2) into intestinal epithelial cell-like cells, wherein step (3) includes culturing in the presence of a MEK1 inhibitor, a DNA methyltransferase inhibitor, a TGF-β receptor inhibitor, and EGF,
    wherein during step (3), at least one agent selected from the group consisting of: exogenous cAMP, exogenous cAMP derivative, and cAMP-degrading enzyme inhibitor is supplied to the cells.

2. The method according to claim 1, wherein step (3) is from 7 days to 40 days of culture.

3. The method according to claim 1, wherein step (3) comprises any one of:
    (A). culturing the intestinal stem cell-like cells in the presence of the MEK1 inhibitor, the DNA methyltransferase inhibitor, the TGF-β receptor inhibitor, and the EGF (a-1), followed by culturing the cells with the presences of the at least one agent (a-2);
    (B). culturing the intestinal stem cell-like cells in the presence of the MEK1 inhibitor, the DNA methyltransferase inhibitor, the TGF-β receptor inhibitor, the EGF and the at least one agent (b-1), followed by culturing in the presence of the MEK1 inhibitor, the DNA methyltransferase inhibitor, the TGF-β receptor inhibitor, the EGF, and a cAMP-degrading enzyme inhibitor (b-2); and
    (C). culturing the intestinal stem cell-like cells in the presence of the MEK1 inhibitor, the DNA methyltransferase inhibitor, the TGF-β receptor inhibitor, the EGF, and the at least one agent simultaneously (c-1).

4. The method according to claim 3, wherein (a-1) ranges from 1 day to 5 days and (a-2) ranges from 3 days to 15 days;
    wherein (b-1) ranges from 3 days to 15 days and (b-2) ranges from 3 days to 15 days; and
    wherein (c-1) ranges from 3 days to 15 days.

5. The method according to claim 3, wherein the at least one agent is cAMP-degrading enzyme inhibitor.

6. The method according to claim 3,
    wherein (A) includes culturing in the presence of the MEK1 inhibitor, the DNA methyltransferase inhibitor, the TGF-β receptor inhibitor, and the EGF (a-3) following (a-2);
    wherein (B) includes culturing in the presence of the MEK1 inhibitor, the DNA methyltransferase inhibitor, the TGF-β receptor inhibitor, and the EGF (b-3) following (b-2); and
    wherein (C) includes culturing in the presence of the MEK1 inhibitor, the DNA methyltransferase inhibitor, the TGF-β receptor inhibitor, and the EGF (c-2) following (c-1).

7. The method according to claim 6, wherein (a-3), (b-3), and (c-2) each range from 1 day to 10 days.

8. The method according to claim 1, wherein the at least one agent is a 8-Br-cAMP.

9. The method according to claim 1, wherein the cAMP-degrading enzyme inhibitor is IBMX.

10. The method according to claim 1, wherein the MEK1 inhibitor is PD98059, the DNA methyltransferase inhibitor is 5-aza-2'-deoxycytidine, and the TGF-β receptor inhibitor is A-83-01.

11. The method according to claim 1, wherein activin A is used as a differentiation inducing factor in step (1).

12. The method according to claim 1, wherein FGF2 is used as a differentiation inducing factor in step (2).

13. The method according to claim 1, wherein the induced pluripotent stem cells are human induced pluripotent stem cells.

* * * * *